(12) United States Patent
Le et al.

(10) Patent No.: US 11,779,728 B2
(45) Date of Patent: Oct. 10, 2023

(54) INTRODUCER SHEATH WITH EXPANDABLE INTRODUCER

(71) Applicant: Edwards Lifesciences Corporation, Irvine, CA (US)

(72) Inventors: Tung T. Le, Costa Mesa, CA (US); Sonny Tran, Westminster, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 292 days.

(21) Appl. No.: 16/690,593

(22) Filed: Nov. 21, 2019

(65) Prior Publication Data

US 2020/0139079 A1    May 7, 2020

Related U.S. Application Data

(63) Continuation of application No. PCT/US2019/058371, filed on Oct. 28, 2019.

(60) Provisional application No. 62/754,516, filed on Nov. 1, 2018.

(51) Int. Cl.
```
A61M 25/00    (2006.01)
A61F 2/24     (2006.01)
A61B 17/00    (2006.01)
A61M 25/06    (2006.01)
```

(52) U.S. Cl.
CPC ..... *A61M 25/003* (2013.01); *A61B 17/00234* (2013.01); *A61F 2/2436* (2013.01); *A61B 2017/00243* (2013.01); *A61M 2025/0681* (2013.01)

(58) Field of Classification Search
CPC ..... A61B 17/00234; A61B 2017/00243; A61F 2/2427; A61F 2/2436; A61F 2/95; A61F 2/962; A61M 2025/0024; A61M 2025/0681; A61M 25/003; A61M 25/0662
See application file for complete search history.

(56) References Cited

U.S. PATENT DOCUMENTS

| | | |
|---|---|---|
| 519,297 A | 5/1894 | Bauer |
| 4,035,849 A | 7/1977 | Angell et al. |
| 4,592,340 A | 6/1986 | Boyles |

(Continued)

FOREIGN PATENT DOCUMENTS

| | | |
|---|---|---|
| DE | 19532846 A1 | 3/1997 |
| DE | 19907646 A1 | 8/2000 |

(Continued)

*Primary Examiner* — Mohamed G Gabr
(74) *Attorney, Agent, or Firm* — Snell & Wilmer LLP; Joel B. German

(57) ABSTRACT

A system for introducing a delivery apparatus into a patient's vasculature. The system may include a sheath having a lumen and configured to be inserted into the patient's vasculature. An introducer has a channel for receiving a guide wire and is configured to be positioned within the lumen of the sheath. A plug is coupled to the introducer and is configured to move from a first position in which the plug has a first diameter to a second position in which the plug has a second diameter that is greater than the first diameter and greater than the interior diameter of the sheath, the plug being configured to slide within the lumen in a direction from the distal end of the sheath towards the proximal end of the sheath to expand the sheath in the direction radially outward from the lumen.

20 Claims, 17 Drawing Sheets

(56) References Cited

U.S. PATENT DOCUMENTS

| | | |
|---|---|---|
| 4,955,895 A | 9/1990 | Sugiyama et al. |
| 4,994,077 A | 2/1991 | Dobben |
| 5,059,177 A | 10/1991 | Towne et al. |
| 5,176,698 A | 1/1993 | Burns et al. |
| 5,192,297 A | 3/1993 | Hull |
| 5,266,073 A | 11/1993 | Wall |
| 5,325,845 A | 7/1994 | Adair |
| 5,358,496 A | 10/1994 | Ortiz et al. |
| 5,411,552 A | 5/1995 | Andersen et al. |
| 5,421,832 A * | 6/1995 | Lefebvre .............. B29C 61/0608 264/DIG. 48 |
| 5,554,185 A | 9/1996 | Block et al. |
| 5,591,195 A | 1/1997 | Taheri et al. |
| 5,599,305 A | 2/1997 | Hermann et al. |
| 5,632,760 A | 5/1997 | Sheiban et al. |
| 5,639,274 A | 6/1997 | Fischell et al. |
| 5,728,068 A | 3/1998 | Leone et al. |
| 5,749,890 A | 5/1998 | Shaknovich |
| 5,782,809 A | 7/1998 | Umeno et al. |
| 5,824,044 A | 10/1998 | Quiachon et al. |
| 5,840,081 A | 11/1998 | Andersen et al. |
| 5,908,405 A | 6/1999 | Imran et al. |
| 5,916,147 A | 6/1999 | Boury |
| 5,961,536 A | 10/1999 | Mickley et al. |
| 5,968,068 A | 10/1999 | Dehdashtian et al. |
| 6,019,777 A | 2/2000 | Mackenzie |
| 6,027,510 A | 2/2000 | Alt |
| 6,033,381 A | 3/2000 | Kontos |
| 6,143,016 A | 11/2000 | Bleam et al. |
| 6,162,208 A | 12/2000 | Hipps |
| 6,168,614 B1 | 1/2001 | Andersen et al. |
| 6,174,327 B1 | 1/2001 | Mertens et al. |
| 6,217,585 B1 | 4/2001 | Houser et al. |
| 6,235,050 B1 | 5/2001 | Quiachon et al. |
| 6,251,092 B1 | 6/2001 | Qin et al. |
| 6,379,372 B1 | 4/2002 | Dehdashtian et al. |
| 6,383,171 B1 | 5/2002 | Gifford et al. |
| 6,454,799 B1 | 9/2002 | Schreck |
| 6,458,153 B1 | 10/2002 | Bailey et al. |
| 6,461,382 B1 | 10/2002 | Cao |
| 6,471,672 B1 | 10/2002 | Brown et al. |
| 6,500,147 B2 | 12/2002 | Omaleki et al. |
| 6,514,228 B1 | 2/2003 | Hamilton et al. |
| 6,527,979 B2 | 3/2003 | Constantz et al. |
| 6,579,305 B1 | 6/2003 | Lashinski |
| 6,582,462 B1 | 6/2003 | Andersen et al. |
| 6,652,578 B2 | 11/2003 | Bailey et al. |
| 6,730,118 B2 | 5/2004 | Spenser et al. |
| 6,733,525 B2 | 5/2004 | Yang et al. |
| 6,764,504 B2 | 7/2004 | Wang et al. |
| 6,767,362 B2 | 7/2004 | Schreck |
| 6,830,584 B1 | 12/2004 | Seguin |
| 6,893,460 B2 | 5/2005 | Spenser et al. |
| 6,908,481 B2 | 6/2005 | Cribier |
| 7,011,094 B2 | 3/2006 | Rapacki et al. |
| 7,018,406 B2 | 3/2006 | Seguin et al. |
| 7,018,408 B2 | 3/2006 | Bailey et al. |
| 7,137,993 B2 | 11/2006 | Acosta et al. |
| 7,276,084 B2 | 10/2007 | Yang et al. |
| 7,318,278 B2 | 1/2008 | Zhang et al. |
| 7,320,702 B2 | 1/2008 | Hammersmark et al. |
| 7,320,704 B2 | 1/2008 | Lashinski et al. |
| 7,374,571 B2 | 5/2008 | Pease et al. |
| 7,393,360 B2 | 7/2008 | Spenser et al. |
| 7,435,257 B2 | 10/2008 | Lashinski et al. |
| 7,510,575 B2 | 3/2009 | Spenser et al. |
| 7,585,321 B2 | 9/2009 | Cribier |
| 7,594,926 B2 | 9/2009 | Linder et al. |
| 7,597,709 B2 | 10/2009 | Goodin |
| 7,618,446 B2 | 11/2009 | Andersen et al. |
| 7,780,723 B2 | 8/2010 | Taylor |
| 7,785,366 B2 | 8/2010 | Maurer et al. |
| 7,959,661 B2 | 6/2011 | Hijlkema et al. |
| 8,029,556 B2 | 10/2011 | Rowe |
| 8,167,932 B2 | 5/2012 | Bourang et al. |
| RE43,882 E | 12/2012 | Hopkins et al. |
| 8,449,606 B2 | 5/2013 | Eliasen et al. |
| 8,475,523 B2 | 7/2013 | Duffy |
| 8,568,472 B2 | 10/2013 | Marchand et al. |
| 9,061,119 B2 | 6/2015 | Le et al. |
| 9,119,716 B2 | 9/2015 | Lee et al. |
| 9,795,477 B2 | 10/2017 | Tran et al. |
| 2001/0002445 A1 | 5/2001 | Vesely |
| 2001/0007082 A1 | 7/2001 | Dusbabek et al. |
| 2002/0032481 A1 | 3/2002 | Gabbay |
| 2002/0058995 A1 | 5/2002 | Stevens |
| 2002/0165461 A1 | 11/2002 | Hayzelden et al. |
| 2003/0040792 A1 | 2/2003 | Gabbay |
| 2003/0050694 A1 | 3/2003 | Yang et al. |
| 2003/0120341 A1 | 6/2003 | Shennib et al. |
| 2004/0093061 A1 | 5/2004 | Acosta et al. |
| 2004/0133263 A1 | 7/2004 | Dusbabek et al. |
| 2004/0143197 A1 | 7/2004 | Soukup et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0080474 A1 | 4/2005 | Andreas et al. |
| 2005/0096736 A1 | 5/2005 | Osse et al. |
| 2005/0137689 A1 | 6/2005 | Salahieh et al. |
| 2005/0149160 A1 | 7/2005 | McFerran |
| 2005/0203614 A1 | 9/2005 | Forster et al. |
| 2005/0203617 A1 | 9/2005 | Forster et al. |
| 2005/0245894 A1 | 11/2005 | Zadno-Azizi |
| 2006/0025857 A1 | 2/2006 | Bergheim et al. |
| 2006/0282150 A1 | 12/2006 | Olson et al. |
| 2007/0005131 A1 | 1/2007 | Taylor |
| 2007/0073389 A1 | 3/2007 | Bolduc et al. |
| 2007/0088431 A1 | 4/2007 | Bourang et al. |
| 2007/0112422 A1 | 5/2007 | Dehdashtian |
| 2007/0203575 A1 | 8/2007 | Forster et al. |
| 2007/0219612 A1 | 9/2007 | Andreas et al. |
| 2007/0239254 A1 | 10/2007 | Chia et al. |
| 2007/0244546 A1 | 10/2007 | Francis |
| 2007/0265700 A1 | 11/2007 | Eliasen et al. |
| 2008/0065011 A1 | 3/2008 | Marchand et al. |
| 2008/0125853 A1 | 5/2008 | Bailey et al. |
| 2008/0294230 A1 | 11/2008 | Parker |
| 2009/0024428 A1 | 1/2009 | Hudock, Jr. |
| 2009/0069889 A1 | 3/2009 | Suri et al. |
| 2009/0138079 A1 | 5/2009 | Tuval et al. |
| 2009/0157175 A1 | 6/2009 | Benichou |
| 2009/0192585 A1 | 7/2009 | Bloom et al. |
| 2009/0221965 A1 * | 9/2009 | Osypka .............. A61M 25/0662 604/160 |
| 2009/0228093 A1 | 9/2009 | Taylor et al. |
| 2009/0276040 A1 | 11/2009 | Rowe et al. |
| 2009/0281619 A1 | 11/2009 | Le et al. |
| 2009/0299456 A1 | 12/2009 | Melsheimer |
| 2009/0319037 A1 | 12/2009 | Rowe et al. |
| 2010/0030318 A1 | 2/2010 | Berra |
| 2010/0036472 A1 | 2/2010 | Papp |
| 2010/0036473 A1 | 2/2010 | Roth |
| 2010/0049313 A1 | 2/2010 | Alon et al. |
| 2010/0076402 A1 | 3/2010 | Mazzone et al. |
| 2010/0076541 A1 | 3/2010 | Kumoyama |
| 2010/0082089 A1 | 4/2010 | Quadri et al. |
| 2010/0094394 A1 | 4/2010 | Beach et al. |
| 2010/0121425 A1 | 5/2010 | Shimada |
| 2010/0145431 A1 | 6/2010 | Wu et al. |
| 2010/0161036 A1 | 6/2010 | Pintor et al. |
| 2010/0174363 A1 | 7/2010 | Castro |
| 2010/0198347 A1 | 8/2010 | Zakay et al. |
| 2010/0274344 A1 | 10/2010 | Dusbabek et al. |
| 2011/0015729 A1 | 1/2011 | Jimenez et al. |
| 2011/0054596 A1 | 3/2011 | Taylor |
| 2011/0137331 A1 | 6/2011 | Walsh et al. |
| 2011/0160846 A1 | 6/2011 | Bishop et al. |
| 2012/0123529 A1 | 5/2012 | Levi et al. |
| 2012/0239142 A1 | 9/2012 | Liu et al. |
| 2013/0030519 A1 | 1/2013 | Tran et al. |
| 2013/0317598 A1 | 11/2013 | Rowe et al. |
| 2014/0296962 A1 | 10/2014 | Cartledge et al. |
| 2017/0065415 A1 | 3/2017 | Rupp et al. |

(56) References Cited

U.S. PATENT DOCUMENTS

2018/0153689 A1    6/2018  Maimon et al.
2018/0200478 A1*   7/2018  Lorenzo ............ A61M 25/0023
2018/0344456 A1   12/2018  Barash et al.

FOREIGN PATENT DOCUMENTS

| | | |
|---|---|---|
| EP | 0592410 B1 | 10/1995 |
| EP | 0850607 A1 | 7/1998 |
| FR | 2815844 A1 | 5/2002 |
| WO | 9117720 A1 | 11/1991 |
| WO | 9829057 A1 | 7/1998 |
| WO | 9912483 A1 | 3/1999 |
| WO | 0149213 A2 | 7/2001 |
| WO | 0154625 A1 | 8/2001 |
| WO | 0176510 A2 | 10/2001 |
| WO | 0222054 A1 | 3/2002 |
| WO | 0236048 A1 | 5/2002 |
| WO | 0247575 A2 | 6/2002 |
| WO | 02060352 | 8/2002 |
| WO | 03030776 A2 | 4/2003 |
| WO | 03047468 A1 | 6/2003 |
| WO | 2004019825 A1 | 3/2004 |
| WO | 2005084595 A1 | 9/2005 |
| WO | 2006032051 A2 | 3/2006 |
| WO | 2006111391 A1 | 10/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2010121076 A2 | 10/2010 |

* cited by examiner

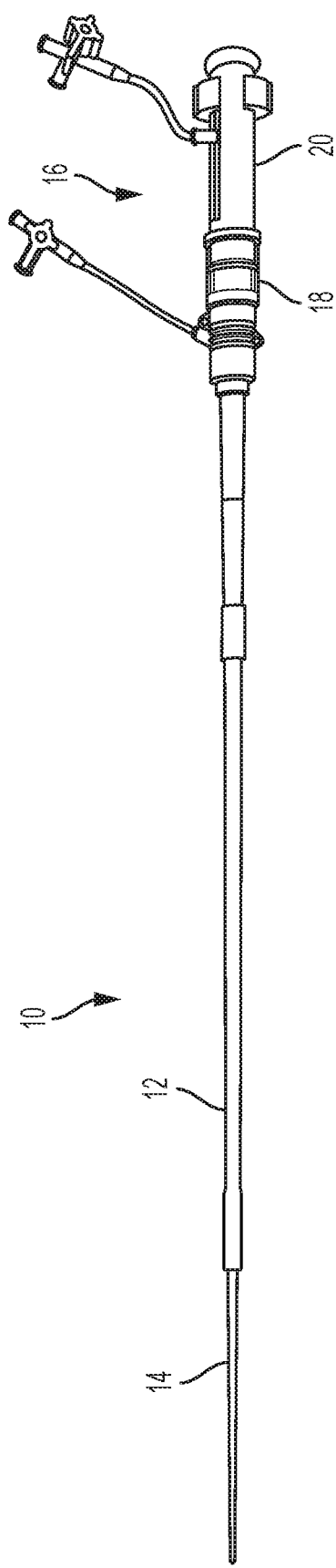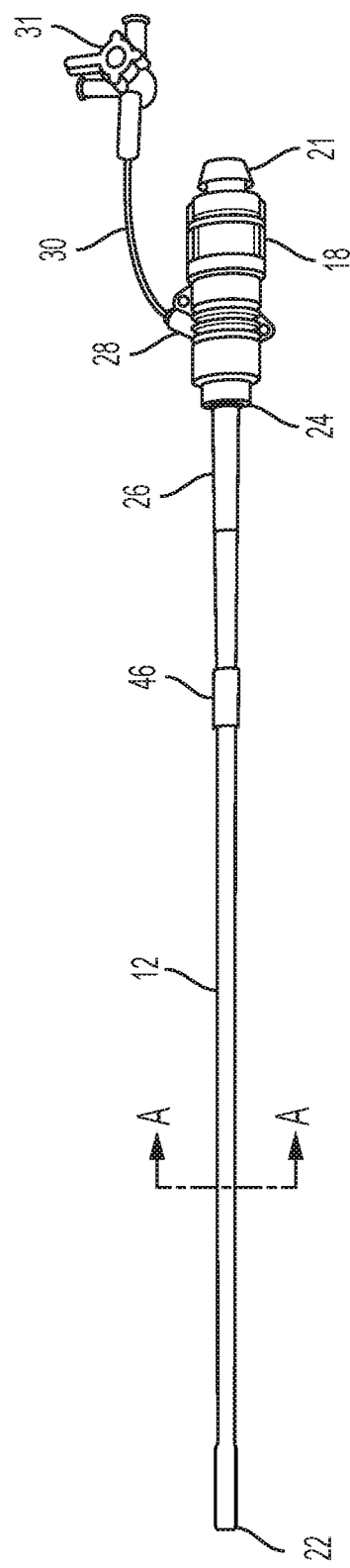
FIG. 1
FIG. 2

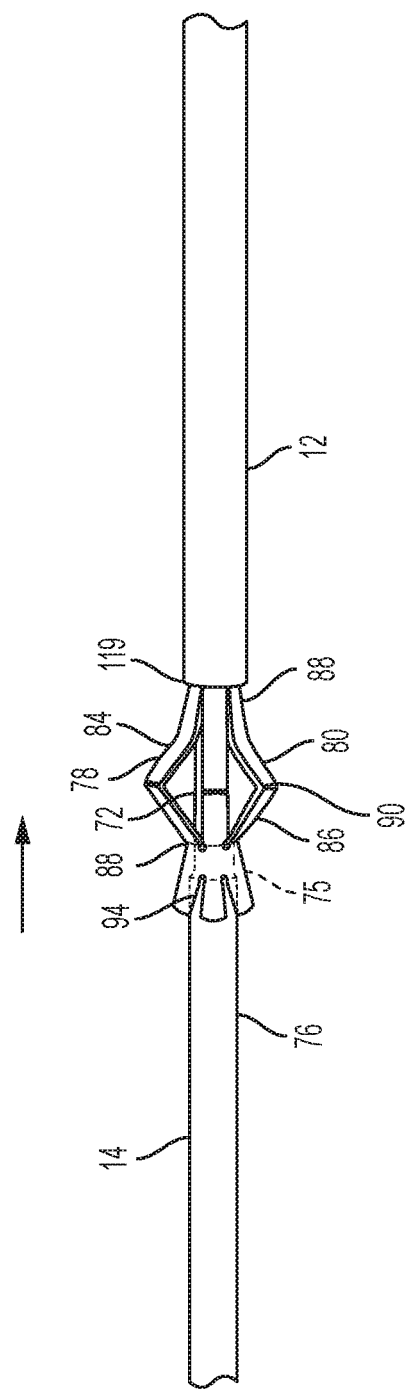

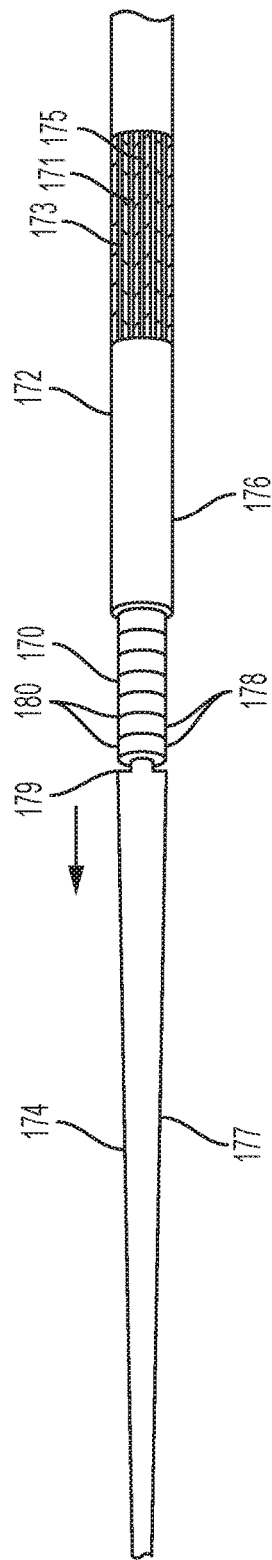
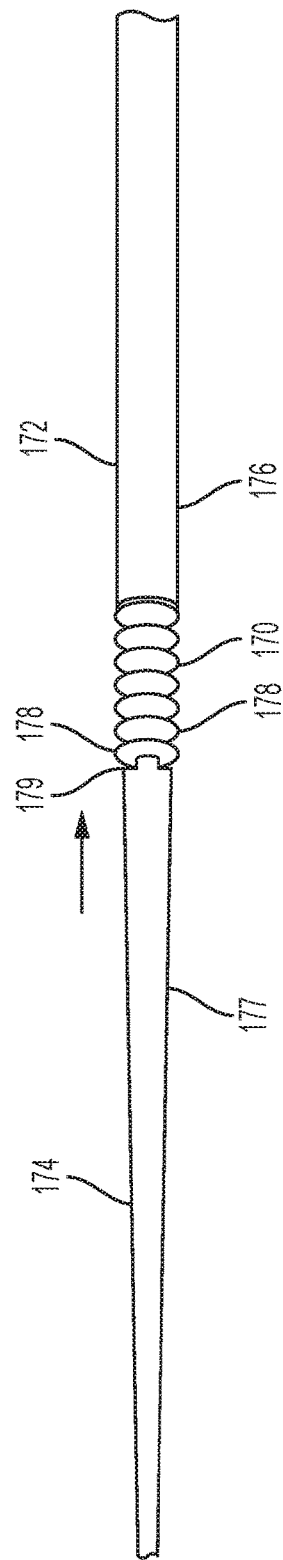
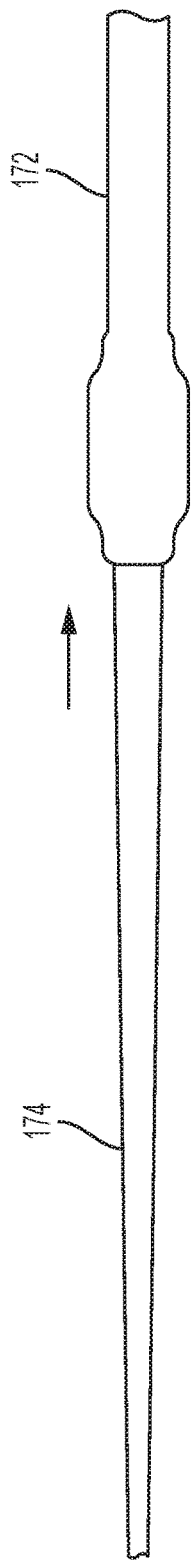
FIG. 15A
FIG. 15B
FIG. 15C

INTRODUCER SHEATH WITH EXPANDABLE INTRODUCER

CROSS-REFERENCE TO RELATED APPLICATIONS

The present application is a continuation of International Application No. PCT/US2019/058371 filed on Oct. 28, 2019, which claims the benefit of U.S. Provisional Patent Application No. 62/754,516 filed on Nov. 1, 2018, both of which are incorporated by reference herein in their entirety.

FIELD

The present application concerns embodiments of a system for introducing a delivery apparatus into a patient's vasculature. The delivery apparatus may comprise a catheter-based technology for repairing and/or replacing heart valves, as well as for delivering an implant, such as a prosthetic heart valve to a heart via the patient's vasculature.

BACKGROUND

Delivery apparatuses are used to implant prosthetic devices, such as a prosthetic heart valve, at locations inside the body that are not readily accessible by surgery or where access without invasive surgery is desirable. For example, aortic, mitral, tricuspid, and/or pulmonary prosthetic heart valves can be delivered to a treatment site using minimally invasive surgical techniques. The delivery apparatuses may comprise endovascular catheter assemblies.

An introducer sheath may be used to introduce a delivery apparatus into a patient's vasculature (e.g., the femoral artery). An introducer sheath generally has an elongated sleeve that is inserted into the vasculature and a housing that contains one or more sealing valves that allow a delivery apparatus to be placed in fluid communication with the vasculature with minimal blood loss.

Conventional methods of accessing a vessel, such as a femoral artery, prior to introducing the delivery apparatus include dilating the vessel using multiple dilators or sheaths that progressively increase in diameter. This repeated insertion and vessel dilation can increase the time the procedure takes, as well as the risk of damage to the vessel.

Accordingly, improvements in systems, apparatuses, and methods of introducing a delivery apparatus into a patient's vasculature are desired.

SUMMARY

The present disclosure is directed to systems, apparatuses, and methods of introducing a delivery apparatus into a patient's vasculature. The system may include a sheath and an introducer positioned therein for introduction to the patient's vasculature. The introducer may include a plug, or an expandable portion of the introducer, for expansion at a position distal of the distal end of the sheath. Upon expansion, the plug, or expandable portion of the introducer, may be withdrawn in a proximal direction through the sheath to expand the sheath prior to insertion of the delivery apparatus. The sheath accordingly may be expanded without requiring insertion of multiple dilators or sheaths that progressively increase in diameter.

The plug, or expandable portion of the introducer, may be integrated into the introducer such that the introducer operates as a standard introducer for the sheath to gain access to the vasculature.

The plug, or expandable portion of the introducer, may be sized such that a transient expansion of the sheath occurs upon the plug being withdrawn through the sheath. The transient expansion may expand a portion of the sheath at a time, to reduce the pulling force required by the plug and to reduce the possibility of the plug being stuck within the sheath. The expansion of the sheath may comprise a preconditioning of the sheath prior to introduction of the delivery apparatus. The preconditioning of the sheath may allow for a lower push force for the delivery apparatus as it is passed through the sheath and into the patient's vasculature.

Embodiments of the present disclosure include a system for introducing a delivery apparatus into a patient's vasculature. The system may include a sheath having a distal end, a proximal end, an interior diameter, a lumen, and a length extending from the distal end to the proximal end. The sheath may be configured to be inserted into the patient's vasculature and to expand in a direction radially outward from the lumen. An introducer may have a channel for receiving a guide wire and may be configured to be positioned within the lumen of the sheath. A plug may be coupled to the introducer and configured to move from a first position in which the plug has a first diameter to a second position in which the plug has a second diameter that is greater than the first diameter and greater than the interior diameter of the sheath, the plug in the first position being configured to fit within the lumen, and the plug in the second position having a length that is less than the length of the sheath and being configured to slide within the lumen in a direction from the distal end of the sheath towards the proximal end of the sheath to expand the sheath in the direction radially outward from the lumen.

Embodiments of the present disclosure include a system for introducing a delivery apparatus into a patient's vasculature. The system may include a sheath having a distal end, a proximal end, an interior diameter, a lumen, and a length extending from the distal end to the proximal end. The sheath may be configured to be inserted into the patient's vasculature and to expand in a direction radially outward from the lumen. An introducer may have a channel for receiving a guide wire and may be configured to be positioned within the lumen of the sheath. The introducer may have an expandable portion including a plurality of supports, the expandable portion configured to move from a first position in which the plurality of supports are flattened and have a first diameter to a second position in which the plurality of supports extend radially outward from the introducer and have a second diameter that is larger than the first diameter and the interior diameter of the sheath, the expandable portion being configured to slide within the lumen in the second position to expand the sheath in the direction radially outward from the lumen.

Embodiments of the present disclosure include a method that may include inserting a guide wire into a patient's vasculature. The method may include inserting a guide wire into a patient's vasculature. The method may include inserting an introducer and a sheath into the patient's vasculature over the guide wire, the sheath extending around the introducer and having a distal end and a proximal end and having a lumen, and being configured to expand in a direction radially outward from the lumen. The method may include activating a plug positioned in the patient's vasculature to move from a first position in which the plug has a first diameter to a second position in which the plug has a second diameter that is greater than an interior diameter of the sheath. The method may include sliding the plug in the second position through the lumen of the sheath in a direction from the distal end of the sheath towards the proximal end of the sheath to expand the sheath in the direction radially outward from the lumen.

BRIEF DESCRIPTION OF THE DRAWINGS

Features and advantages of the systems, apparatuses, and methods as disclosed herein will become appreciated as the same become better understood with reference to the specification, claims, and appended drawings wherein:

FIG. 1 illustrates a side view of a system according to an embodiment of the present disclosure.

FIG. 2 illustrates a side view of the sheath shown in FIG. 1.

FIG. 9 illustrates a close-up side view of the distal end of the sheath and the introducer shown in FIG. 1.

FIG. 15A illustrates a side view of a portion of a system according to an embodiment of the present disclosure, with a portion cut away.

FIG. 15B illustrates a side view of the portion of system shown in FIG. 15A.

FIG. 15C illustrates a side view of the portion of system shown in FIG. 15A.

DETAILED DESCRIPTION

Figure 3:
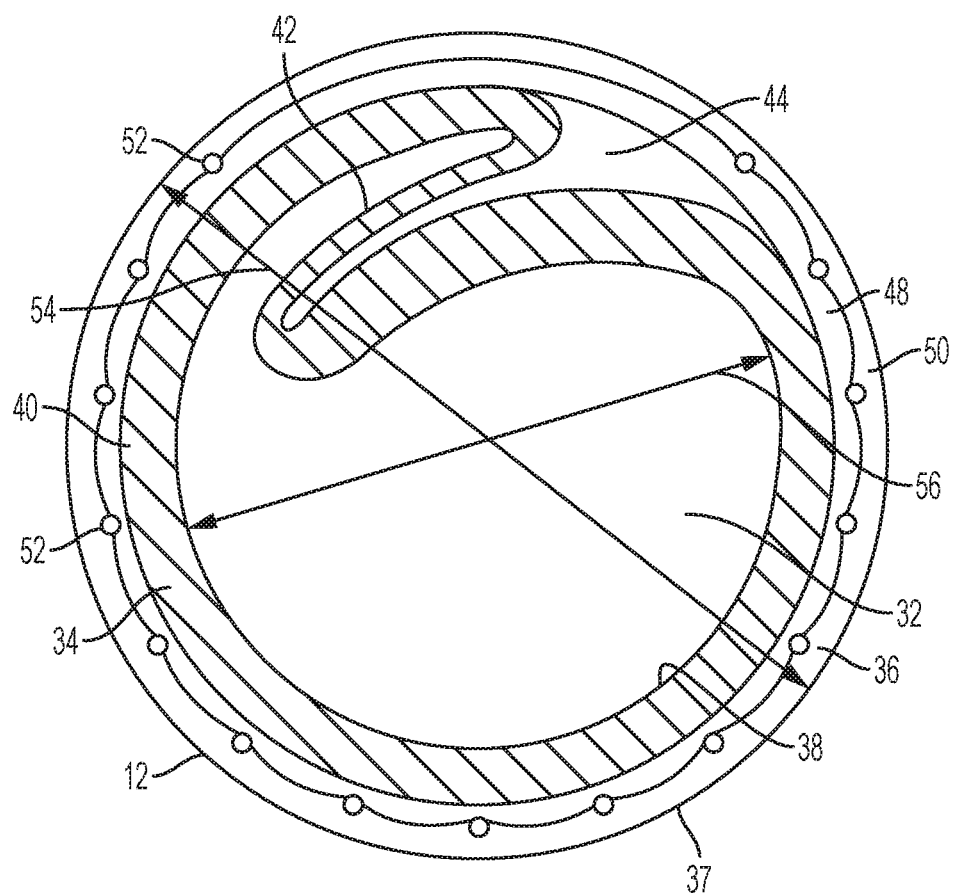
FIG. 3 illustrates a cross sectional view of the sheath shown in FIG. 2 along line A-A in FIG. 2.

FIG. 1 illustrates an embodiment of a system 10 for introducing a delivery apparatus into a patient's vasculature. The system 10 may include a sheath 12 and an introducer 14. The introducer 14 may be positioned within a lumen of the sheath 12, as shown in FIG. 1. A control housing 16 may be positioned at a proximal end of the system and may include a sheath housing 18 and an introducer housing 20. The sheath housing 18 and introducer housing 20 may couple together, as shown in FIG. 1.

The sheath 12 and introducer 14 are shown in an insertion configuration, for insertion together into the patient's vasculature. Upon insertion into the patient's vasculature, the introducer 14 may be withdrawn longitudinally from the sheath 12, leaving the sheath 12 within the patient's vasculature. Features of the sheath 12 and the introducer 14 individually are discussed below, as well as the operation of the sheath 12 and introducer 14 together.

FIG. 2 illustrates the sheath 12 separated from the introducer 14. The sheath 12 comprises an elongate body that may have a cylindrical shape. The sheath 12 has a distal end 22 and a proximal end 24 and a length extending from the distal end 22 to the proximal end 24.

The sheath 12 is configured to be inserted into a patient's vasculature. The sheath 12 may comprise an introducer sheath that is used to introduce a delivery apparatus into the patient's vasculature.

The vasculature may comprise the blood vessels of the patient's body which may include the femoral artery or other vessels of the patient's body. The vasculature, such as the femoral artery, may be narrow or stiff, and may be difficult to easily insert a delivery apparatus therein. For example, the delivery apparatus may be larger than the vasculature, or may be unwieldy to penetrate through the skin or vasculature of the patient to pass therethrough by itself. Also, the vasculature may be too fragile to receive the delivery apparatus without use of an introducer sheath.

The sheath 12 accordingly may be inserted into the patient's vasculature prior to the delivery apparatus being introduced, to provide an entryway or guide path for the delivery apparatus to introduce the delivery apparatus into the patient's vasculature. After the sheath 12 is inserted, the sheath 12 may remain positioned within and surrounded by the patient's vasculature. The delivery apparatus may then be passed through the lumen of the sheath 12 for introduction into the patient's body. The sheath 12 may remain in the vasculature until a desired time to remove the sheath 12.

The sheath 12 may be inserted into the vasculature percutaneously or a portion of the patient's body may be surgically opened for the sheath 12 to access the vasculature.

Figure 18:
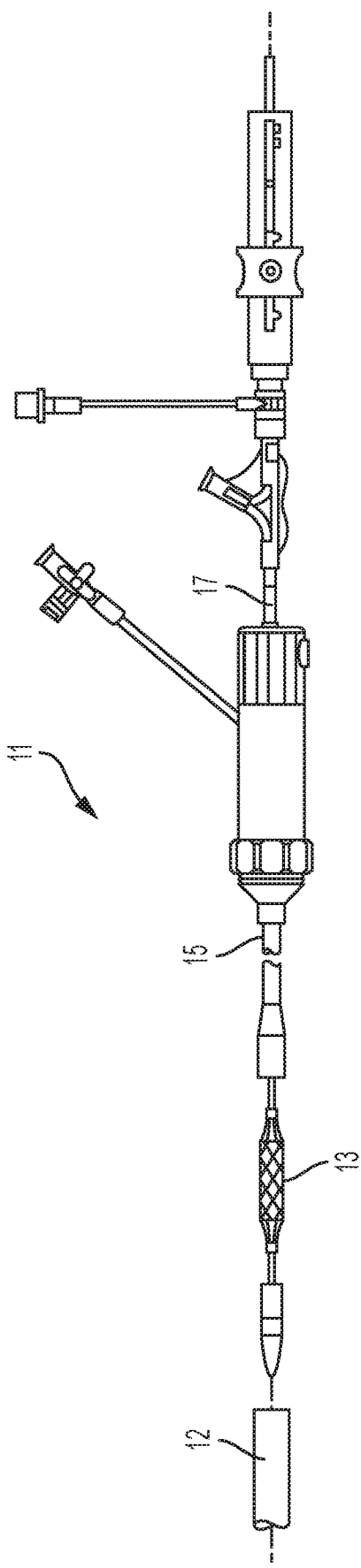
FIG. 18 illustrates a side view of a delivery apparatus, according to an embodiment of the present disclosure.

The delivery apparatus may be configured in a manner such as the delivery apparatus 11 shown in FIG. 18. The delivery apparatus 11 may comprise a device for delivering an implant 13, or other type of implantable device, to a patient. The delivery apparatus 11 may comprise a catheter, and may include a steerable guide catheter 15 (also referred to as a flex catheter) and a balloon catheter 17 extending through the guide catheter 15. The guide catheter 15 and the balloon catheter 17 may be adapted to slide longitudinally relative to each other to facilitate delivery and positioning of the implant 13 at an implantation site in the patient's body. The delivery apparatus 11 may comprise an endovascular catheter assembly for endovascular deployment of the implant 13.

The implant 13 may comprise a prosthetic device, such as a prosthetic heart valve to be delivered to replace a heart valve of the patient. The prosthetic heart valve may be an aortic, mitral, tricuspid, and/or pulmonary heart valve for implantation. The prosthetic heart valve may be an expandable heart valve that is passed through the patient's vasculature in an undeployed configuration and then is expanded into a deployed configuration when placed in the desired position (e.g., at the heart valve to be replaced). The delivery apparatus 11 may be configured to pass through the patient's vasculature to deliver the implant 13 to the desired location (e.g., the location of the heart valve to be replaced). Upon being placed in the desired position, a deployment device, such as the balloon of the balloon catheter 17 may deploy the heart valve in position. In other embodiments, other forms of implants may be utilized, such as stents or filters, or diagnostic devices, among others. In other embodiments, other forms of delivery apparatuses than shown in FIG. 18 may be utilized.

The delivery apparatus 11 passes through the lumen of the sheath 12 to reach a desired position in the patient's body. As shown in FIG. 18, the delivery apparatus 11 may pass through an opening at the proximal end of the sheath 12 (the sheath housing 18 is not shown in FIG. 18) for passage through the lumen of the sheath 12 and the vasculature of the patient.

The delivery apparatus and the systems disclosed herein may be used in transcatheter aortic valve implantation (TAVI). The delivery apparatus and the systems disclosed herein may be utilized for transarterial access, including transfemoral access, to a patient's heart.

Referring back to FIG. 2, the sheath housing 18 may be positioned at the proximal end 24 of the sheath 12. The sheath housing 18 may comprise a cylindrical body and may include a coupler 21 for coupling to another housing or component of the system. The sheath housing 18 may include an internal chamber 19 (marked in FIG. 7) for the delivery apparatus 11 to be passed through to be delivered to the patient's vasculature. The sheath housing 18 may be configured to remain external to the patient's vasculature when the sheath 12 is inserted therein and may be configured to remain external to the patient's skin for a percutaneous implantation of the sheath 12. The sheath housing 18 may be configured for a user (such as a surgeon) to grip to manipulate the sheath 12.

The sheath 12 may include a strain relief portion 26 at the proximal end 24 of the sheath 12. The strain relief portion 26 may be sized larger than a proximate portion of the sheath 12 and may seal the entry point of the vasculature, to reduce the possibility of blood or other fluid being released between the exterior surface of the sheath 12 and the vasculature. The sheath housing 18 may include a fluid port 28 for passing fluid such as blood to or from the patient's vasculature. Tubing 30 with a valve 31 may be coupled to the fluid port 28, for passing fluid through the fluid port 28 and for sealing flow of the fluid through the fluid port 28.

FIG. 3 illustrates a cross sectional view of the sheath 12 along line A-A in FIG. 2. The sheath 12 has a lumen 32 and one or more walls surrounding the lumen 32. In the embodiment shown in FIG. 3, the walls may include an inner tubing wall 34 that surrounds the lumen 32 and an outer tubing wall 36 that surrounds the inner tubing wall 34.

The inner tubing wall 34 may have an interior surface that comprises the interior surface 38 of the sheath 12. The inner tubing wall 34 may include a thick portion 40 and a thin portion 42. The inner tubing wall 34 may be folded upon itself such that a fold exists at the thin portion 42, as shown in FIG. 3. The fold may result in a channel 44 being positioned between the inner tubing wall 34 and the outer tubing wall 36. A seal 46 (marked in FIG. 2) may be positioned along the length of the sheath 12 to prevent blood or other fluid flow from passing through the channel 44 and out of the proximal end 24 of the sheath 12.

The outer tubing wall 36 may have an exterior surface that comprises the exterior surface 37 of the sheath 12. The outer tubing wall 36 may include multiple layers, including an inner layer 48 and an outer layer 50 extending around the inner layer 48.

Reinforcements 52 may be provided in the sheath 12. The reinforcements 52 may comprise elongate rods that may be positioned between the inner layer 48 and the outer layer 50 of the outer tubing wall 36 and may extend along the length of the sheath 12. The reinforcements 52 may provide strength to the sheath 12.

The sheath 12 may have an outer diameter 54 and an interior diameter 56. The outer diameter 54 may be the diameter of the exterior surface 37 of the sheath, and the interior diameter 56 may be the diameter of the interior surface 38 of the sheath 12.

The sheath 12 may be configured to expand in a direction radially outward from the lumen 32. The sheath 12 may be configured to expand in a variety of manners, and may be flexible in a direction radially outward from the lumen 32. For example, in the embodiment shown in FIG. 3, the inner tubing wall 34 and the outer tubing wall 36 may each be configured to expand in a direction radially outward from the lumen 32. The inner tubing wall 34 and the outer tubing wall 36 may both be flexible to allow for expansion in the direction radially outward from the lumen 32.

The inner tubing wall 34 may be configured such that the thin portion 42 is more flexible than the thick portion 40 and accordingly fully or partially unfolds to expand the fold when a force is applied to the inner tubing wall 34 radially outward from the lumen 32. The unfolding of the inner tubing wall 34 allows the inner tubing wall 34 to expand in the direction radially outward from the lumen 32. The outer tubing wall 36 may be stretchable and may correspondingly expand in the direction radially outward from the lumen 32 by the force of the inner tubing wall 34 pressing against the outer tubing wall 36.

The expansion of the sheath 12 in the direction radially outward from the lumen 32 may result in an increased size of the lumen 32, the interior diameter 56, and the outer diameter 54.

In other embodiments, other manners of expansion may be utilized, for example stretchable walls or walls that are otherwise flexible may be utilized without the use of a fold or channel in a wall of the sheath 12, or other methods may be utilized. In one embodiment, a compressible wall may be utilized to expand the sheath 12. The sheath 12 may expand by the interior diameter 56 being increased in size, or both the interior diameter 56 and outer diameter 54 being increased in size.

The sheath 12 may be configured for a localized expansion, in which the expansion occurs at a location where an object is passing therethrough.

The sheath 12 may be configured to expand to allow for a relatively low-profile, or narrow outer diameter 54, insertion into the patient's vasculature. The narrow outer diameter 54 may be sized to fit within the patient's vasculature with relatively low insertion push force. The narrow outer diameter 54, however, may correspond to a narrow interior diameter 56. The narrow interior diameter 56 may be too narrow to receive the delivery apparatus 11 or may result in relatively high insertion push force to be provided by the delivery apparatus 11. The expansion of the sheath 12 in the direction radially outward from the lumen 32 increases the interior diameter 56 of the sheath 12 and may thus reduce the insertion push force that is needed for the delivery apparatus 11.

The sheath 12 may be elastic, and may be biased in a direction towards the lumen 32. The sheath 12 accordingly may attempt to contract or otherwise reduce in size. The reduction in size may occur in a variety of manners. For example, in the embodiment shown in FIG. 3, the outer tubing wall 36 may be elastic and configured to apply a force in a direction radially towards the lumen 32 upon being forced in a direction radially outward from the lumen 32 by the inner tubing wall 34. The outer tubing wall 36, upon expansion, may apply a compressive force to the inner tubing wall 34. This compressive force may serve to reduce the size of the lumen 32 and the interior diameter 56 of the sheath 12. In other embodiments, the entirety of the sheath wall may be elastic and biased in the direction radially towards the lumen 32. In other embodiments, other means may be utilized to bias the sheath 12 in the direction towards the lumen 32.

The sheath 12 may be configured such that the elastic restoring force of the sheath 12 does not fully move the sheath 12 back to its pre-expanded size. For example, in the embodiment shown in FIG. 3, the sheath 12 is shown in a pre-expanded configuration. The sheath 12 has an interior diameter 56. The sheath may be expanded by an object being passed through the lumen 32 of the sheath that has a diameter larger than the interior diameter 56 of the sheath 12. Upon the sheath 12 being expanded, the interior diameter 56 will increase to a larger size (due to the larger diameter of the object). The outer diameter 54 may also increase to a larger size. Upon the object being passed through the sheath 12, the sheath 12 may elastically return towards the lumen 32, but not fully back to the size or diameter shown in FIG. 3. The resulting interior diameter 56 of the sheath may be larger than the diameter in the pre-expanded configuration, but not larger that its diameter when the object is passing through. Similarly, the resulting outer diameter 54 may be larger than the diameter in the pre-expanded configuration, but not larger that its diameter when the object is passing through. Thus, the sheath 12 may be configured for a partial return to its pre-expanded configuration and size.

The sheath 12 may be configured to be elastic (e.g., partially return to a pre-expanded configuration) to allow for a reduction in the size of the outer diameter 54 upon the delivery apparatus 11 being passed therethrough. The reduced size of the outer diameter 54 may allow for ease of removal of the sheath 12 from the patient's vasculature and reduced stress being applied to the vasculature when the delivery apparatus 11 is not positioned within the sheath 12.

Figure 4:
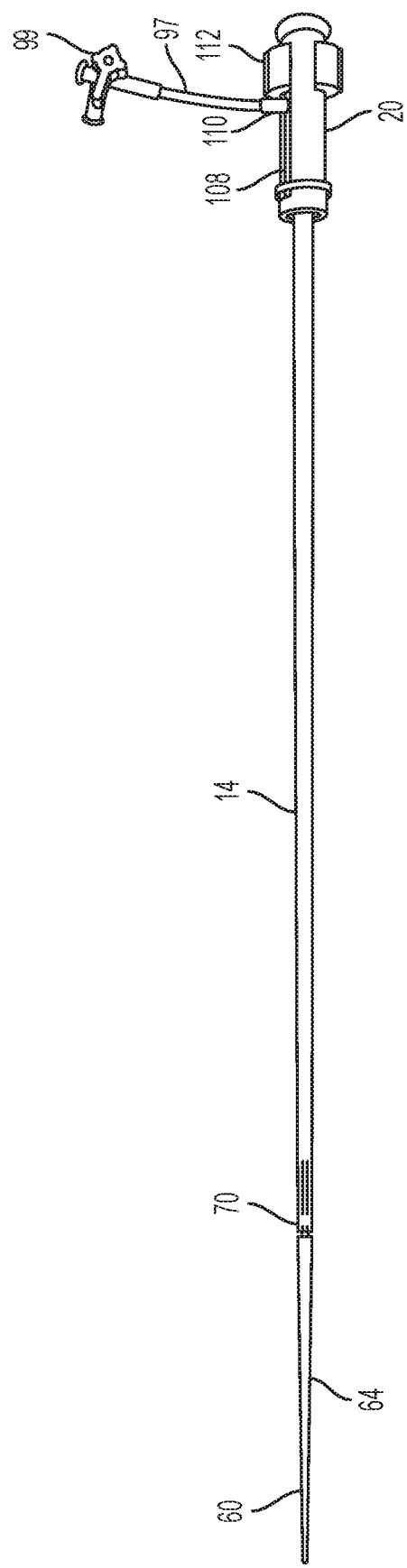
FIG. 4 illustrates a side view of the introducer shown in FIG. 1.

Referring to FIG. 4, the introducer 14 may be utilized to introduce the sheath 12 into the vasculature of the patient's body. The introducer 14 is configured to be positioned within the lumen of the sheath 12 to introduce the sheath 12 into the vasculature of the patient's body, as shown in FIG. 1.

Figure 7:
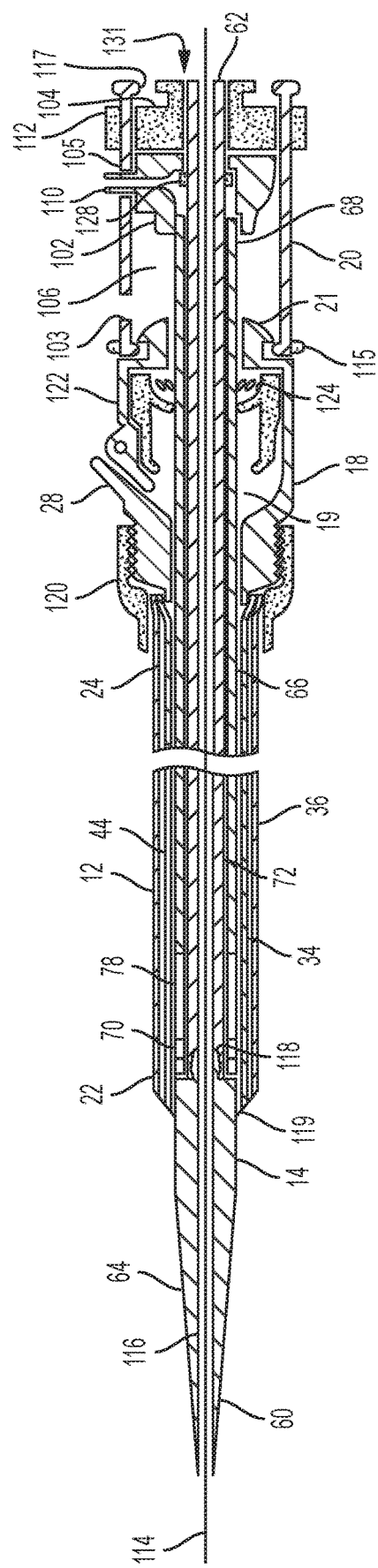
FIG. 7 illustrates a cross sectional view of the system shown in FIG. 1 along a midline of the system.

FIG. 4 illustrates the introducer 14 separated from the sheath 12. The introducer 14 comprises an elongate body having a distal end 60, a proximal end 62 (marked in FIG. 7) and a length extending from the distal end 60 to the proximal end 62. The introducer 14 may be configured to have a length that is greater than the length of the sheath 12, such that a portion of the introducer 14 extends beyond the distal end 22 of the sheath 12 (marked in FIG. 2). The introducer 14 may include a tip 64. The tip 64 may be tapered down to the distal end 60 of the introducer 14. The tapered distal tip 64 may be configured to extend beyond the distal end 22 of the sheath 12 when the introducer 14 is positioned within the lumen of the sheath 12, as shown in FIGS. 1 and 7.

The introducer 14 may include an outer shaft 66 (marked in FIGS. 5 and 7) that extends along a length of the introducer 14. The outer shaft 66 may have a proximal end 68 (marked in FIG. 7) and a distal end 70 and a length extending from the distal end 70 to the proximal end 68. The outer shaft 66 may comprise a tube extending around a portion of the introducer, such that the portion of the introducer 14 that is within the outer shaft 66 comprises an inner shaft 72 (marked in FIGS. 5 and 7) and such that the outer shaft 66 comprises an outer tube. The introducer 14 may comprise a two-part shaft (inner shaft 72 and outer shaft 66).

Figure 5:
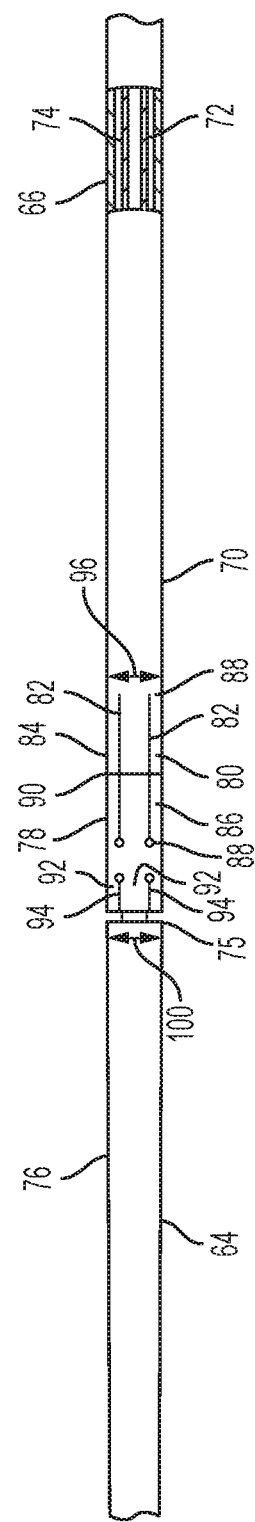
FIG. 5 illustrates a close-up side view of the distal end of the introducer shown in FIG. 4.

FIG. 5 illustrates a close-up view of the distal end 70 of the outer shaft 66, with a portion cut away to show the inner shaft 72 within the outer shaft 66. The inner shaft 72 portion may comprise a portion 74 of the introducer and the tip 64 may comprise a thicker portion 76 of the introducer 14 such that the portion 74 is a thin portion 74 and the portion 76 is a thick portion 76. The introducer 14 may transition between the inner shaft 72 portion to the thick portion 76 at a step 75.

A plug 78 may be coupled to the introducer 14. The plug 78 may comprise an expandable portion of the introducer 14. The plug 78 accordingly may be integral with the introducer 14. The plug 78 may comprise a plurality of supports 80. The plurality of supports 80 may be separated from each other by a respective slit 82 or other form of separation between the supports 80. The supports 80 may comprise slats that are separated by slits 82. The supports 80 and slits 82 may extend longitudinally along the introducer 14.

The supports 80 may include proximal supports 84 and distal supports 86, each of which may be configured to pivot at pivot portions 88 of the plug 78. The proximal supports 84 and distal supports 86 may couple to each other at a pivot portion 90 of the plug 78, which may be a central pivot portion 90. The pivot portions 88, 90 however, may be unpivoted, or flattened, in the position shown in FIG. 5.

A distal portion of the plug 78 may include additional supports 92 separated by slits 94.

The plug 78 may be configured to be integral with the outer shaft 66, as shown in FIG. 5. The supports 80 may each be integral with the outer shaft 66. The slits 82, 94 may comprise slits in the outer shaft 66. As such, the plug 78 may be a portion of the outer shaft 66, and may be activated by manipulation of the outer shaft 66.

The plug 78 may be configured to move from a first position in which the plug 78 has a first diameter to a second position in which the plug 78 has a second diameter that is greater than the first diameter. The plug 78 is shown in FIG. 5 in a first position, in which the plug 78 is flattened, or in an unexpanded configuration or undeployed configuration.

Figure 10A:
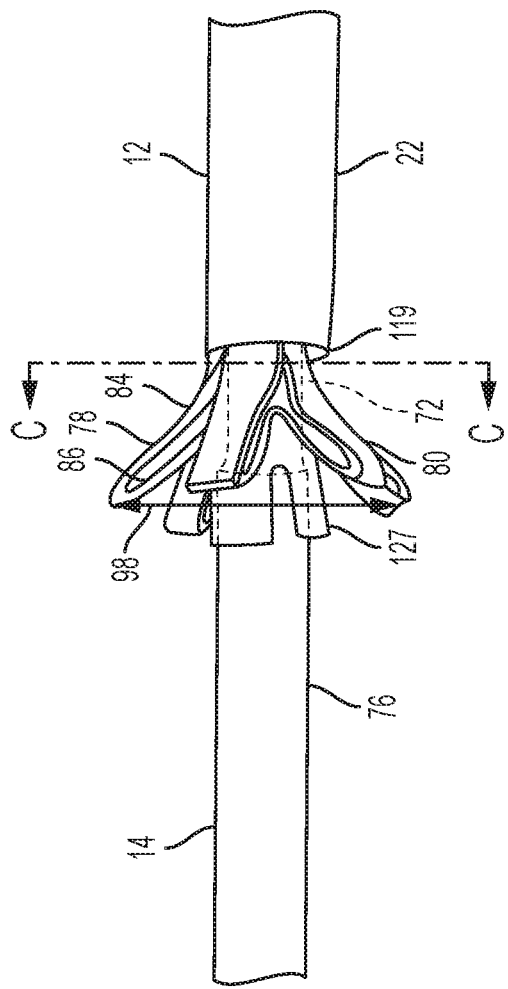
FIG. 10A illustrates a close-up side view of the distal end of the sheath and the introducer shown in FIG. 1.

The supports 80 extend along the longitudinal axis of the introducer 14 and around the inner shaft 72 of the introducer 14. The plug 78 has a diameter 96 in the first position. The plug 78 may move to a second position, as shown in FIG. 10A, in which the plug 78 is in an expanded configuration, or deployed configuration, and has a diameter 98 that is greater than the diameter 96, and greater than the interior diameter 56 of the sheath 12 (marked in FIG. 3). The supports 80 in the second position extend radially outward from the introducer 14.

The plug 78 in the first position may be configured to fit within the lumen 32 of the sheath 12. The plug 78 may have a diameter 96 that is sized to fit within the lumen 32 of the sheath 12. The diameter 96 may be substantially equal to or less than to the diameter 100 of the thick portion 76 of the introducer 14 (which is the outer diameter of the introducer 14). Thus, the plug 78 in the first position may fit within the lumen 32 without increasing the size of the lumen 32 or otherwise expanding the sheath 12. The diameter 100 of the introducer 14 may be configured to be at or less than the interior diameter 56 of the sheath 12.

Figure 6:
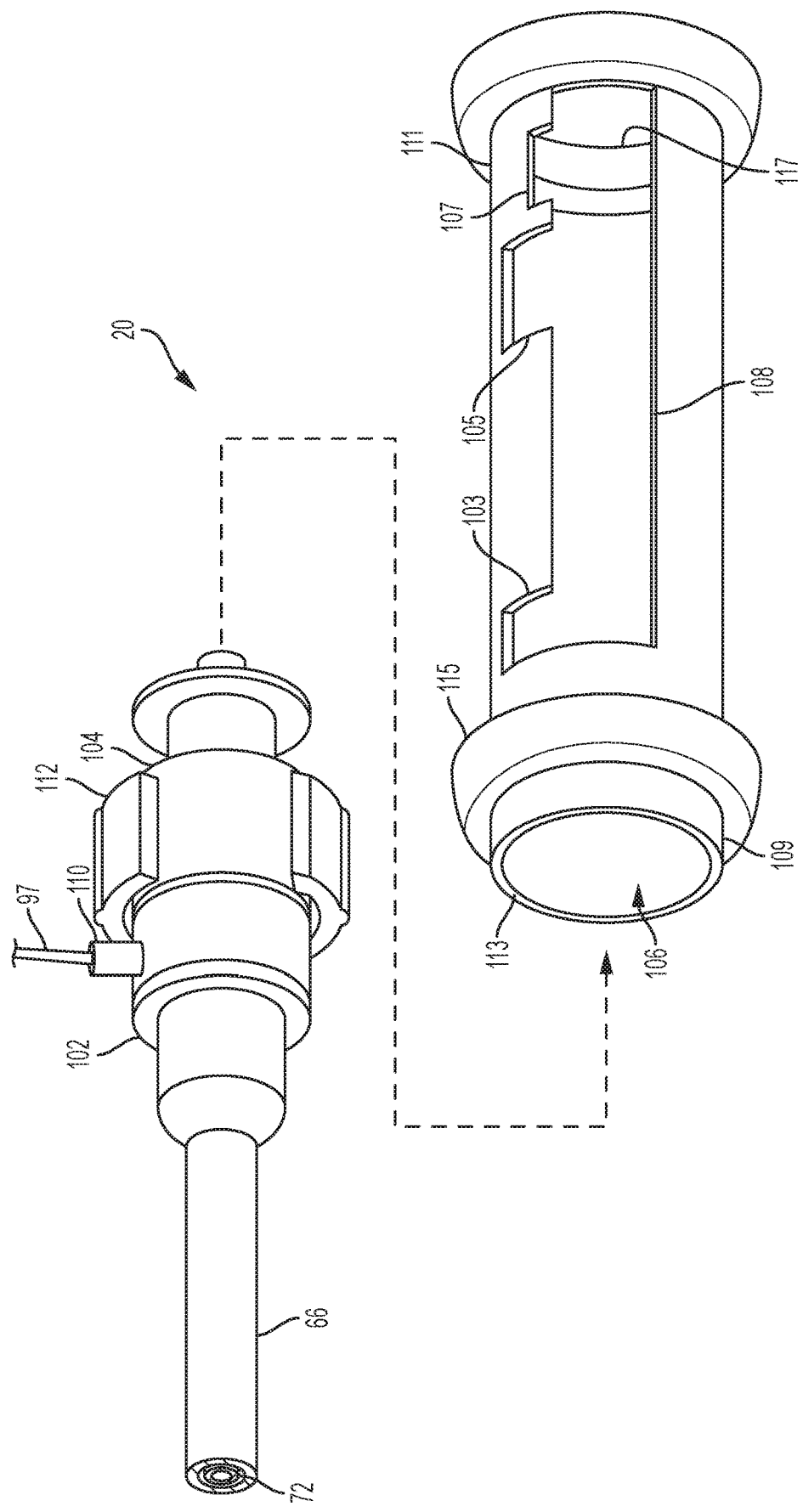
FIG. 6 illustrates a close-up perspective side view of the introducer housing shown in FIG. 4 disassembled, with an inner shaft and an outer shaft shown in cross-section.

Referring to FIGS. 4 and 6, the introducer housing 20 may be positioned at the proximal end of the introducer 14. FIG. 6 illustrates a disassembled view of the introducer housing 20, with the outer shaft 66 and inner shaft 72 shown in cross section. An outer shaft housing 102 and an inner shaft housing 104 are shown separated from an interior chamber 106 of the introducer housing 20.

The introducer housing 20 may be configured to couple to the sheath housing 18. The introducer housing 20 may be configured as a control device for controlling the introducer 14 and the plug 78. The introducer housing 20 may include an interior chamber 106. The introducer housing 20 may include a slide channel 108 and locks 103, 105, 107. The slide channel 108 may be configured as a cut-out in the body of the introducer housing 20, and the locks 103, 105, 107 may be configured as cut-outs in the body of the introducer housing 20 in a transverse direction as the slide channel 108.

The introducer housing 20 may include a distal end 109 and a proximal end 111 and a length extending from the distal end 109 to the proximal end 111. The distal end 109 may include an opening 113 that extends around a portion of the sheath housing 18, particularly the coupler 21 (marked in FIG. 2). A securing device such as a securing ring 115 may extend over the body of the introducer housing 20 at the coupler 21 to couple the introducer housing 20 to the sheath housing 18. The proximal end 111 of the introducer housing 20 may include an opening 117 for a guide wire 114 (marked in FIG. 7) to extend through. The introducer housing 20 may be configured for a user (such as a surgeon) to grip to manipulate the introducer 14 and the plug 78.

The introducer housing 20 may include an outer shaft housing 102 and an inner shaft housing 104. The outer shaft housing 102 and the inner shaft housing 104 may be positioned within the interior chamber 106 of the introducer housing 20. The outer shaft housing 102 and the inner shaft housing 104 may be configured to move relative to each other to control the plug 78 and separately control the outer shaft 66 and the inner shaft 72.

The outer shaft housing 102 may couple to the proximal end 68 of the outer shaft 66 (marked in FIG. 7). The outer shaft housing 102 may include a fluid port 110 for passing fluid such as blood to or from the patient's vasculature. Tubing 97 with a valve 99 (marked in FIG. 4) may be coupled to the fluid port 110 for passing fluid through the fluid port 110 and for sealing flow of the fluid through the fluid port 110.

The outer shaft housing 102 may be configured to move relative to the body of the introducer housing 20 and relative to the sheath housing 18 and the inner shaft housing 104, such that the outer shaft housing 102 and the outer shaft 66 may move relative to the inner shaft 72 and the sheath 12.

The outer shaft housing 102 may be configured to slide longitudinally within the interior chamber 106 of the introducer housing 20 with the fluid port 110 extending through the slide channel 108. The outer shaft housing 102 may also be configured to rotate within the body of the introducer housing 20 around the longitudinal axis that the outer shaft 66 extends along. The outer shaft housing 102 may be configured to rotate around this longitudinal axis to have the fluid port 110 rotate in and out of the lock 103 and lock 105.

The inner shaft housing 104 may couple to the proximal end 62 (marked in FIG. 7) of the inner shaft 72. The inner shaft housing 104 may include a control surface 112 that may be positioned exterior of the body of the introducer housing 20 when the inner shaft housing 104 is positioned within the interior chamber 106 of the introducer housing 20. The connection between the body of the inner shaft housing 104 and the control surface 112 may extend through the slide channel 108, such that the body of the inner shaft housing 104 is within the interior chamber 106 and the control surface 112 is exterior. The control surface 112 may be configured for a user (such as a surgeon) to manipulate to control the inner shaft 72 and the plug 78.

The inner shaft housing 104 may be configured to move relative to the body of the introducer housing 20 and relative to the sheath housing 18 and the outer shaft housing 102, such that the inner shaft housing 104 and the inner shaft 72 may move relative to the outer shaft 66 and the sheath 12.

The inner shaft housing 104 may be configured to slide longitudinally within the interior chamber 106 of the introducer housing 20. The inner shaft housing 104 may also be configured to rotate within the body of the introducer housing 20 around the longitudinal axis that the inner shaft 72 extends along. The inner shaft housing 104 may be configured to rotate around this longitudinal axis to have the connection between the body of the inner shaft housing 104 and the control surface 112 rotate in and out of the lock 105 and lock 107.

The introducer 14 is configured to be inserted into, and positioned within the lumen 32 of the sheath 12, upon the introducer 14 and sheath 12 being introduced into the patient's vasculature. The introducer 14 preferably comprises a rigid body with sufficient strength to guide the sheath 12 into the patient's vasculature, with sufficient flexibility to allow for flexible movements of the introducer 14 and sheath 12 together. The tapered tip 64 of the introducer is preferably shaped to improve ease of penetration and access of the patient's vasculature by opening the interior of the vasculature as the introducer 14 and sheath 12 together are inserted into the vasculature. The tip 64 may be configured to be soft and flexible to reduce the possibility of damaging the patient's vasculature.

The sheath 12 and introducer 14 may be configured to be held in an insertion configuration in which the sheath 12 is positioned around the introducer 14 when introduced into the patient's vasculature. An insertion configuration is shown in FIG. 1. The sheath 12 and introducer 14 may be held in position relative to each other by the coupling between the sheath housing 18 and the introducer housing 20. The tip 64 of the introducer 14 extends beyond the distal end 22 of the sheath 12. The introducer 14 is held in position relative to the sheath 12 such that a length of the introducer 14 extends beyond the distal end 22 of the sheath 12 and the plug 78 is within the lumen of the sheath 12. This position of the introducer 14 and the plug 78 relative to the sheath 12 may be referred to as an insertion position, for introduction into the patient's vasculature.

The sheath 12 and introducer 14 in the insertion configuration may be introduced into the patient's vasculature by being slid over a guide wire 114 (marked in FIG. 7) that has been previously introduced into the patient's vasculature. The sheath 12 in this configuration is preferably sized to fit within the vasculature of the patient, and has a relatively low profile, or narrow outer diameter.

FIG. 7 illustrates a cross sectional view of the system shown in FIG. 1 along a midline of the system.

As shown in FIG. 7, the introducer 14, including the inner shaft 72 of the introducer 14, may include an internal channel 116 that extends along its length, from the distal end 60 of the introducer 14 to the proximal end 62 of the introducer 14 (the proximal end of the inner shaft 72). The channel 116 is configured to receive a guide wire 114 that the introducer 14 extends over when the introducer 14 is inserted into the vasculature of the patient's body.

The tip 64 of the introducer 14 may couple to the inner shaft 72 portion of the introducer 14 via a threaded connection 118. In other embodiments, other forms of connections may be utilized.

The outer shaft 66 is shown to extend over the inner shaft 72 from the distal end 70 of the outer shaft 66 to the proximal end 68 of the outer shaft 66. The plug 78 is in the first position and positioned within the sheath 12.

The outer tubing wall 36 of the sheath 12 is shown extending over the inner tubing wall 34 of the sheath 12, which accordingly extends over the introducer 14 and the plug 78. The channel 44 of the sheath 12 is shown extending proximally from the distal end 22 of the sheath 12. The sheath 12 at the distal end 22 may be configured with a taper to allow for a smooth tapered transition between the introducer 14 and the sheath 12 at a distal opening 119 of the sheath 12. The distal opening 119 may be at the distal end 22 of the sheath 12 and configured for the introducer 14 and plug 78 to pass therethrough.

The proximal end 24 of the sheath 12 may couple to an outer housing 120, or distal housing, of the sheath housing 18. The outer housing 120 may be threaded or otherwise coupled to an inner housing 122, or proximal housing, of the sheath housing 18. The inner housing 122 may include the interior chamber 19 that may transfer fluids to or from the system, for example, via the fluid port 28, and may receive the introducer 14, including the inner shaft 72 and outer shaft 66. A movable wall 124 comprising a plurality of flaps may be positioned in the interior chamber 19 and may form a seal around the introducer 14 when the introducer 14 is positioned within the sheath 12 and passes through the movable wall 124.

The introducer housing 20 is shown coupled to the coupler 21. The introducer housing 20 may be positioned over the coupler 21. The securing ring 115 may extend over the introducer housing 20 at the coupler 21 to couple the introducer housing 20 to the sheath housing 18 with a press fit or the like.

The outer shaft housing 102 is shown positioned within the interior chamber 106 of the introducer housing 20. A seal 128 may be positioned within the outer shaft housing 102 and may seal the connection between the outer shaft housing 102 and the inner shaft 72 such that fluid does not leak when the outer shaft housing 102 moves relative to the inner shaft 72.

The outer shaft housing 102 in FIG. 7 is locked in position relative to the other components of the system. The locked position in FIG. 7 is caused by the fluid port 110 being positioned in the lock 105. The locked position prevents the outer shaft housing 102 and the outer shaft 66 from sliding relative to other components of the system.

The inner shaft housing 104 is shown to include an internal channel 131 that allows the guide wire 114 and the proximal end 62 of the introducer 14 to pass therethrough.

The inner shaft housing 104 in FIG. 7 is locked in position relative to the other components of the system. The locked position in FIG. 7 is caused by the connection between the body of the inner shaft housing 104 and the control surface 112 being positioned in the lock 107 (the lock 107 is shown in FIG. 6). The locked position prevents the inner shaft housing 104 and the inner shaft 72 from sliding relative to other components of the system.

The system shown in FIG. 7 is in a configuration for insertion into the patient's vasculature. The components are preferably locked in position relative to each other such that the components do not slide or otherwise move relative to each other upon insertion, aside from the system sliding along the guide wire 114.

Upon the system being placed in the desired position within the patient's body, the plug 78 may be activated from the first position to the second position and the introducer 14 may be withdrawn from the sheath 12. Such an operation leaves the sheath 12 in position within the patient's vasculature, in position to introduce a delivery apparatus (such as delivery apparatus 11 shown in FIG. 18).

Figure 8A:
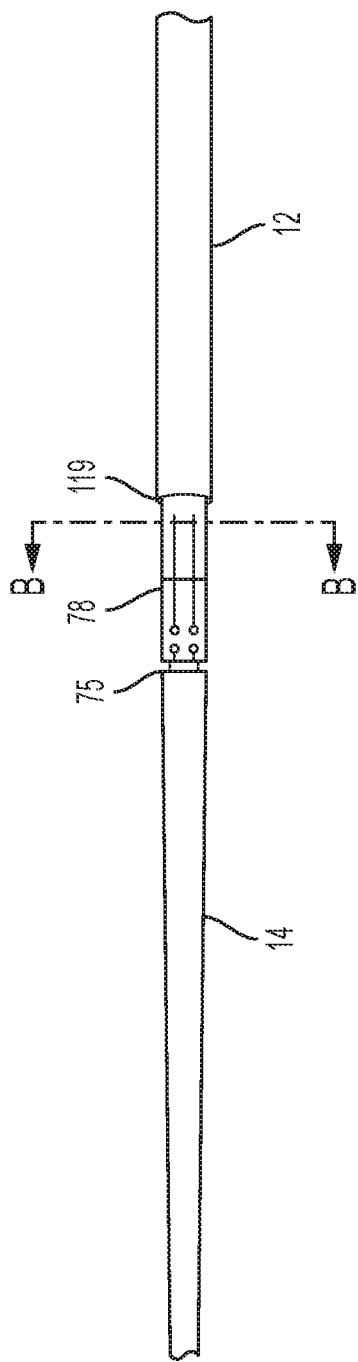
FIG. 8A illustrates a close-up side view of the distal end of the sheath and the introducer shown in FIG. 1.
Figure 8B:
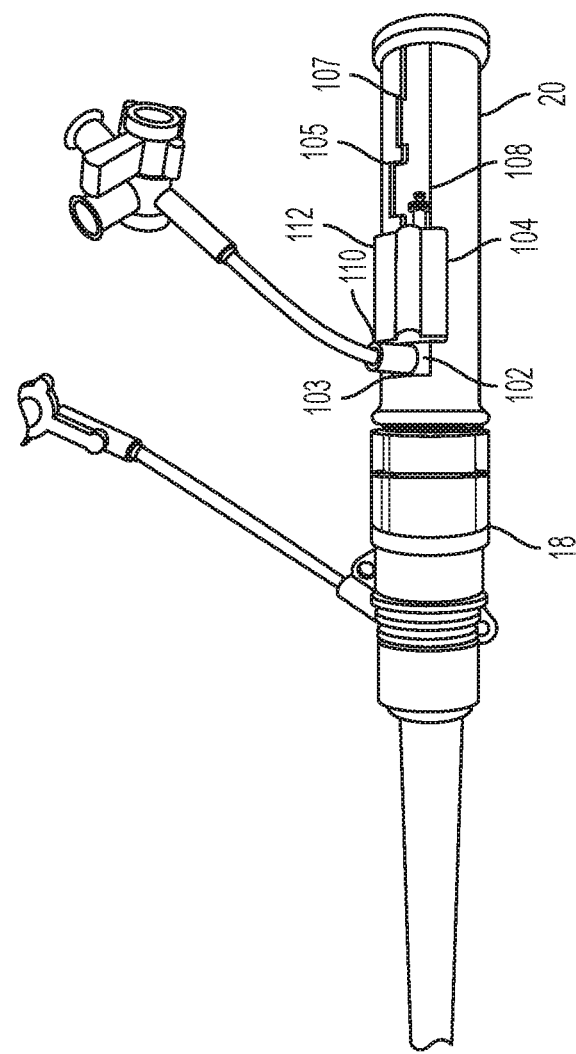
FIG. 8B illustrates a close-up side view of the control housing shown in FIG. 1.

FIGS. 8A and 8B illustrate a step in the movement of the plug 78 from the first position to the second position. In FIG. 8A, the introducer 14 and plug 78 have been moved to an advanced configuration, in an advanced position distally beyond the opening 119 of the sheath 12. The introducer 14 and plug 78 have slid distally relative to the sheath 12. The sliding movement of the introducer 14 and plug 78 may be by a defined distance. The introducer 14 and plug 78 slide relative to the guide wire 114 (shown in FIG. 7). The plug 78 preferably remains in the first position during this movement to the advanced position. Preferably the sheath 12 does not slide within the patient's vasculature during this movement. In an embodiment in which the plug 78 is coupled to, or a part of the outer shaft 66, the outer shaft 66 may slide relative to the sheath 12 as well to move the plug 78 into the desired position.

Figure 13B:
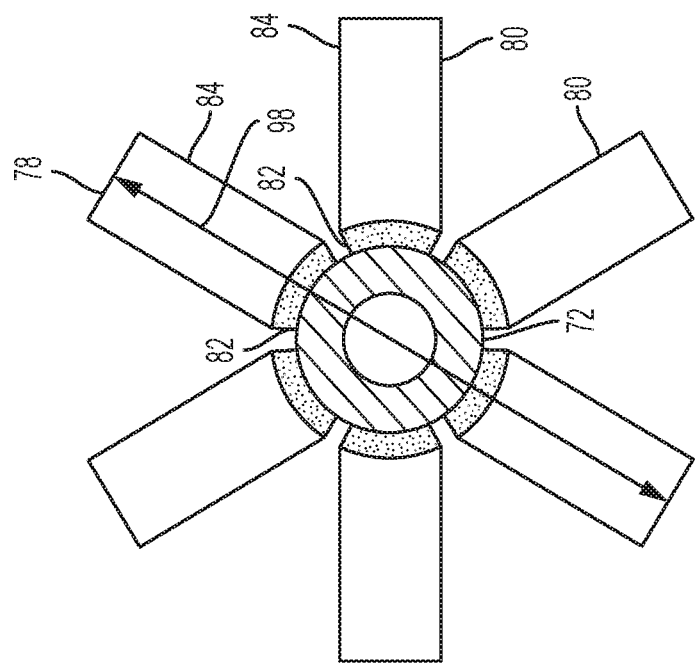
FIG. 13B illustrates a cross sectional view of introducer shown in FIG. 10A along line C-C in FIG. 10A.
Figure 13A:
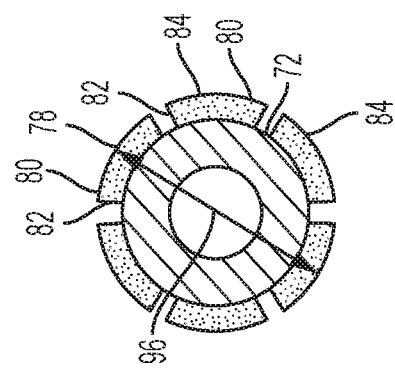
FIG. 13A illustrates a cross sectional view of introducer shown in FIG. 8A along line B-B in FIG. 8A.

Referring to FIG. 13A, a cross sectional view of the introducer 14 is shown along line B-B in FIG. 8A. The plurality of supports 80 are shown to extend along the inner shaft 72 and are separated by slits 82.

The movement of the introducer 14 and plug 78 in FIG. 8A may be produced by the movement of the outer shaft housing 102 and the inner shaft housing 104 relative to the body of the introducer housing 20. FIG. 8B shows the movement of the housings 102, 104. In FIG. 8B, the outer shaft housing 102 has released from the lock 105 by being rotated out of the lock 105. The outer shaft housing 102 may rotate around the longitudinal axis that the outer shaft 66 extends along to rotate out of the lock 105. The inner shaft housing 104 may also rotate out of the lock 107. Upon both housings 102, 104 being unlocked, they may each slide longitudinally within the introducer housing 20 and slide distally to the distal end of the slide channel 108. The housings 102, 104 may slide a defined length to correspondingly extend the introducer 14 and plug 78 the defined length from the opening 119 of the sheath 12 shown in FIG. 8A. The introducer 14 accordingly may be sized to have a length that is greater than the sheath 12 by at least the length of the plug 78 in the first position, to allow the plug 78 to be slid out from the end of the sheath 12. The outer shaft housing 102, and particularly the fluid port 110, may rotate within the introducer housing 20 to lock into lock 103.

Upon the outer shaft housing 102 being locked into lock 103, the outer shaft 66 and accordingly the plug 78 may be held in position relative to the sheath 12. The inner shaft 72, however, may be able to slide proximally relative to the outer shaft 66, the plug 78, and the sheath 12. This movement may be available because the inner shaft housing 104 is not locked relative to the introducer housing 20. The inner shaft housing 104 may slide longitudinally proximally relative to the introducer housing 20, with the outer shaft housing 102 being locked into lock 103, to retract the inner shaft 72 relative to the plug 78.

FIG. 9 illustrates a view of the inner shaft 72 of the introducer 14 being partially retracted, or partially slid proximally, relative to the plug 78. The plug 78 is in an intermediate position between the first position (as represented in FIG. 8A) and the second position (as represented in FIG. 10A). The arrow shown in FIG. 9 illustrates the movement of the inner shaft 72 of the introducer 14 relative to the plug 78. A portion of the introducer 14, for example the step 75 of the introducer 14, may press against the plug 78 in the proximal direction to apply a force to the plug 78. The force of the introducer 14 applied by the introducer 14 to the plug 78 causes the plug to move from the first position to the second position. The force of the introducer 14 against the plug 78 may cause the distal portion of the plug 78 to overlap the thick portion 76 of the introducer 14. The slits 94 may allow for expansion of the distal portion such that the distal portion flares open and may form an angled portion of the plug 78 tapering outward in the distal direction.

The supports 80 may bow outward from the inner shaft 72 of the introducer 14. The proximal supports 84 and distal supports 86 may each pivot at opposite angles relative to each other. The proximal supports 84 and distal supports 86 may each pivot about respective pivot portions 88, 90.

The inner shaft 72 of the introducer 14 may continue to slide proximally relative to the sheath 12 and outer shaft 66 until the inner shaft 72 of the introducer 14 reaches a position shown in FIG. 10A. The plug 78 may be positioned on the introducer 14 such that the plug 78 moves from the first position to the second position at a position distal the opening 119 of the sheath 12, and exterior of the lumen of the sheath 12, when the introducer 14 is positioned within the lumen 32. The introducer 14 has continued to apply a force against the plug 78 in the proximal direction until the proximal supports 84 have overlapped the distal supports 86. The distal supports 86 have folded under the respective proximal supports 84. The supports 80 are configured to bend to move the plug 78 from the first position to the second position. The respective supports 80 overlap upon itself in the second position. The supports in this configuration form a plurality of protrusions extending outward from the introducer 14. The distal portion of the plug 78 that overlaps the thick portion 76 of the introducer 14 forms a bump 127 that the supports 84, 86 are positioned over, and the bump 127 supports the supports 84, 86 to increase the diameter 98 of the plug 78. The supports 84, 86 together form a conical shape tapering outward in the distal direction. The plug 78 in this position (the second position) has a diameter 98 that is greater than the diameter 96 of the plug in the first position (as shown in FIG. 5), and is greater than the interior diameter 56 of the sheath 12, as is marked in FIG. 3. The plug 78 in this position is in a deployed configuration, or expanded configuration.

The plug 78 in the second position extends radially outward from the introducer 14. The plug 78 in the second position has a length that is less than the length of the sheath 12 and is configured to slide within the lumen 32 in a direction from the distal end 22 of the sheath 12 towards the proximal end 24 of the sheath 12 to expand the sheath 12 in a direction radially outward from the lumen 32. The length of the plug 78 in the second position may, in one embodiment, be less than 2% the length of the sheath 12. The length of the plug 78 in the second position may in one embodiment be less than 5% the length of the sheath 12. The length of the plug 78 in the second position may in one embodiment be less than 10% the length of the sheath 12. The length of the plug 78 in the second position in other embodiments may be less than 20%, 30%, 40% or 50% the length of the sheath 12, among other lengths. The plug 78 may be positioned on the introducer 14 such that the entirety of the plug 78 in the second position is closer to the distal end 60 of the introducer 14 than the proximal end 62 of the introducer 14.

Referring to FIG. 13B, a cross sectional view of the introducer 14 is shown along line C-C in FIG. 10A. The plurality of supports 80 are shown to extend outward radially from the inner shaft 72. The number of supports 80 is shown to be six in FIG. 13B, however, in other embodiments the number may be greater or lesser. In one embodiment, one support may be utilized.

Figure 10B:
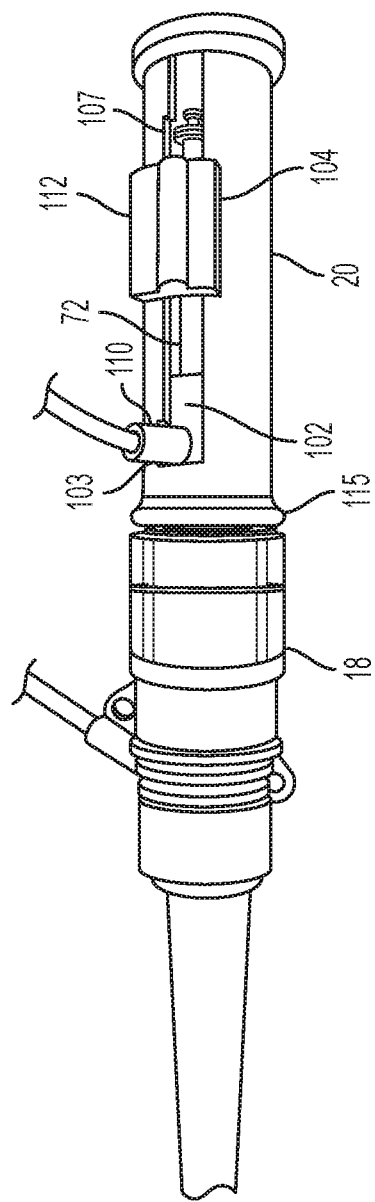
FIG. 10B illustrates a close-up side view of the control housing shown in FIG. 1.

FIG. 10B illustrates the position of the outer shaft housing 102 and the inner shaft housing 104 relative to the introducer housing 20 when the plug 78 is in the position shown in FIG. 10A. The introducer housing 20 remains coupled to the sheath housing 18. The outer shaft housing 102 remains locked in the lock 103. The inner shaft housing 104, however, has slid proximally relative to the outer shaft housing 102 and has been placed into lock 105 by being rotated into lock 105. The distance between the outer shaft housing 102 and the inner shaft housing 104 may be a defined distance, defining a relative distance of movement between the inner shaft 72 of the introducer 14 and the plug 78.

Upon the plug 78 being moved to the second position, and the outer shaft housing 102 and the inner shaft housing 104 being locked in position in the introducer housing 20, the introducer housing 20 may be released from the sheath housing 18. The securing device such as the securing ring 115 may be released and the introducer housing 20 may be pulled proximally from the sheath housing 18. The plug 78 may enter the opening 119 of the sheath 12 and slide relative to the sheath 12 within the lumen of the sheath 12.

Figure 11A:
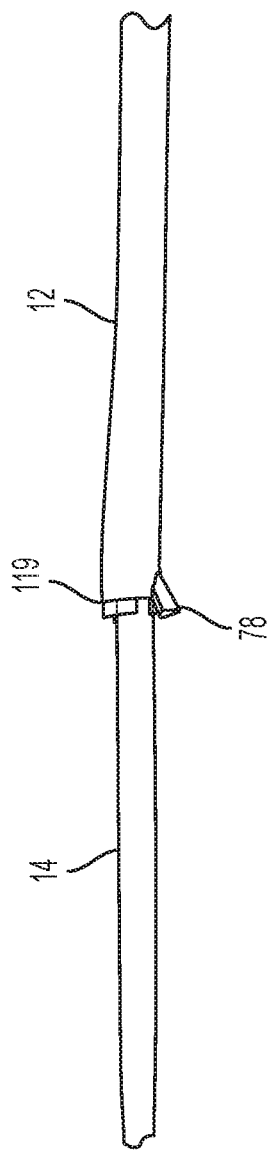
FIG. 11A illustrates a close-up side view of the distal end of the sheath and the introducer shown in FIG. 1.
Figure 11B:
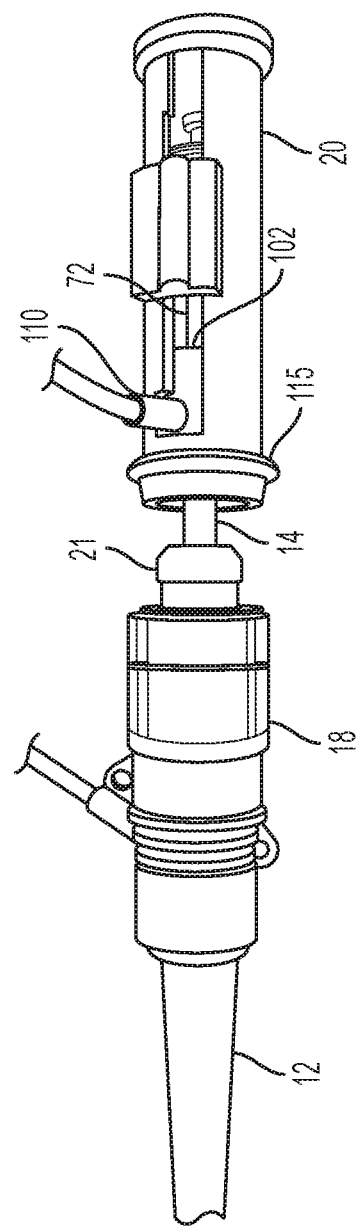
FIG. 11B illustrates a close-up side view of the control housing shown in FIG. 1.

FIG. 11A illustrates the plug 78 and introducer 14 being slid proximally within the lumen of the sheath 12. The plug 78 has entered the opening 119 of the sheath 12. FIG. 11B illustrates the configuration of the introducer housing 20 in which the introducer housing 20 is released from the sheath housing 18 and moved proximally. The movement of the introducer housing 20 retracts or withdraws the introducer 14 from the sheath 12, while leaving the sheath 12 in place within the patient's vasculature.

The increased diameter of the plug 78 in the second position, as the plug 78 is slid proximally through the sheath's 12 lumen causes the sheath 12 to expand. The interior diameter 56 and lumen 32 (marked in FIG. 3) of the sheath 12 are increased by the radial pressing force applied by the plug 78 to the interior surface 38 of the sheath 12 (also marked in FIG. 3).

The plug 78 preferably has a length that is less than the length of the sheath 12, such that as the plug 78 is slid proximally through the lumen of the sheath 12, a transient expansion of the sheath 12 occurs. Thus, only a portion of the sheath 12 has a force applied to it and has a localized expansion caused by the plug 78 at a given moment. The plug 78 may be coupled to the introducer 14 such that withdrawal of the introducer 14 through the lumen 32 in the proximal direction causes the plug 78 to enter the opening 119 of the sheath 12 and slide within the lumen 32 in the proximal direction to transiently expand the sheath 12 in the direction radially outward from the lumen 32. The transient force to a portion of the sheath 12 allows for a lesser force to be applied to the sheath 12 than if the entirety of the sheath 12 were expanded at once. In addition, the sliding motion of the plug 78 reduces static friction that may exist between the plug 78 and the interior surface of the sheath 12. The sliding motion also reduces the possibility of the plug 78 becoming stuck in the lumen, due to the kinetic energy provided to the plug 78 and the reduction of adhesive forces that may exist between the outer surface of the plug 78 and the interior surface of the sheath if the plug 78 were deployed within the lumen.

Figure 12A:
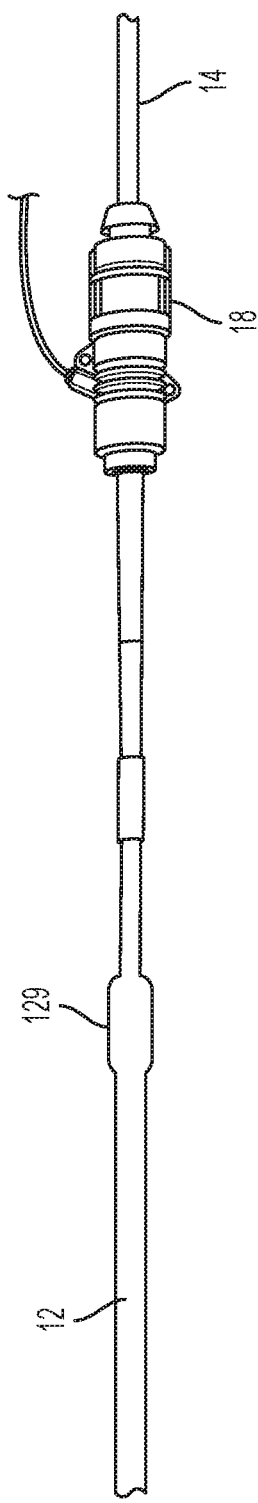
FIG. 12A illustrates a side view of the system shown in FIG. 1.
Figure 12B:
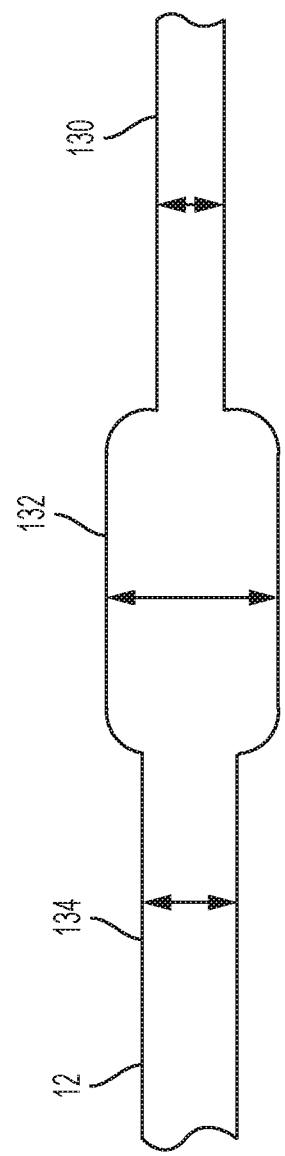
FIG. 12B illustrates a schematic view of a portion of a sheath shown in FIG. 1.

FIG. 12A illustrates the transient expansion of the sheath 12. The plug 78 is being slid proximally relative to the sheath 12. The location of the plug 78 within the sheath is marked in FIG. 12A as reference number 129. The plug 78 may expand the sheath 12 at the position of the plug 78 and may leave an increased size in the sheath 12 in the distal portion of the sheath 12. FIG. 12B illustrates a representation of the movement of the plug 78 within the sheath 12. In FIG. 12B, the plug 78 has not yet passed through the proximal portion of the sheath 12 marked as portion 130. The plug 78 is within the portion of the sheath 12 marked as portion 132. The plug 78 has passed through the portion of the sheath 12 marked as portion 134. The diameter of the sheath 12 at portion 132 is larger than in portion 130 because the plug 78 has not yet passed through portion 130. The diameter of the sheath 12 at portion 134 may be less than the diameter at portion 132 because the sheath may be elastic and biased in a direction radially towards the lumen. The plug 78 accordingly may be configured to transiently expand a distal portion of the sheath 12, and then a central portion of the sheath 12, and then a proximal portion of the sheath 12 in successive order, rather than expanding a distal, central, and proximal portion of the sheath 12 all at one time. The plug 78 may be sized or have a length relative to the length of the sheath 12 to only expand a portion of the sheath 12 at one time.

The sheath 12 may be configured to partially return to a pre-expanded configuration, as discussed previously. The difference in diameter between portion 134 and portion 130, however, may decrease the insertion push force of a delivery apparatus inserted through the sheath 12 after the introducer 14 and plug 78 have been removed from the sheath 12.

The plug 78 and introducer 14 may continue to be withdrawn from the sheath 12 until completely removed from the lumen of the sheath 12. Upon their removal, a delivery apparatus such as the apparatus 11 shown in FIG. 18 may be inserted into the sheath 12 in a distal direction with a reduced pushing force due to the expanded lumen size.

The system allows for insertion of the sheath 12 and the introducer 14 into the patient's vasculature with a relatively low-profile, or narrow outer diameter. As the introducer 14 is removed from the sheath 12 to leave the sheath 12 positioned within the patient's vasculature, the plug 78 serves to expand the sheath 12, providing a larger lumen 32 size and larger interior diameter 56. The sheath 12 may partially return to a pre-expanded configuration upon the plug passing therethrough (as marked as portion 134 in FIG. 12B), however, the enhanced size of the sheath 12 nonetheless reduces insertion push force required for the delivery apparatus to be inserted through the sheath 12. The sheath 12 accordingly may be preconditioned for introduction of the delivery apparatus via a plug 78 integrated with the introducer 14.

The system provides benefits over prior methods of sheath expansion. In prior methods, once the introducer (without a plug) is removed from the sheath, one or more dilator rods may be inserted through the sheath in the distal direction to progressively expand the size of the sheath. These prior methods may include multiple steps (e.g., insert sheath and introducer, remove introducer, insert and remove multiple dilator rods) before insertion of the delivery apparatus. The system may alleviate these issues by allowing removal of the introducer with the expanded plug to expand the sheath, without multiple dilator rods needing to be inserted into the sheath. The system may thus provide a reduced number of steps during a medical procedure.

In other prior methods, the delivery apparatus is simply pushed through the sheath without the sheath being pre-expanded by a dilator rod or otherwise.

Figure 17:
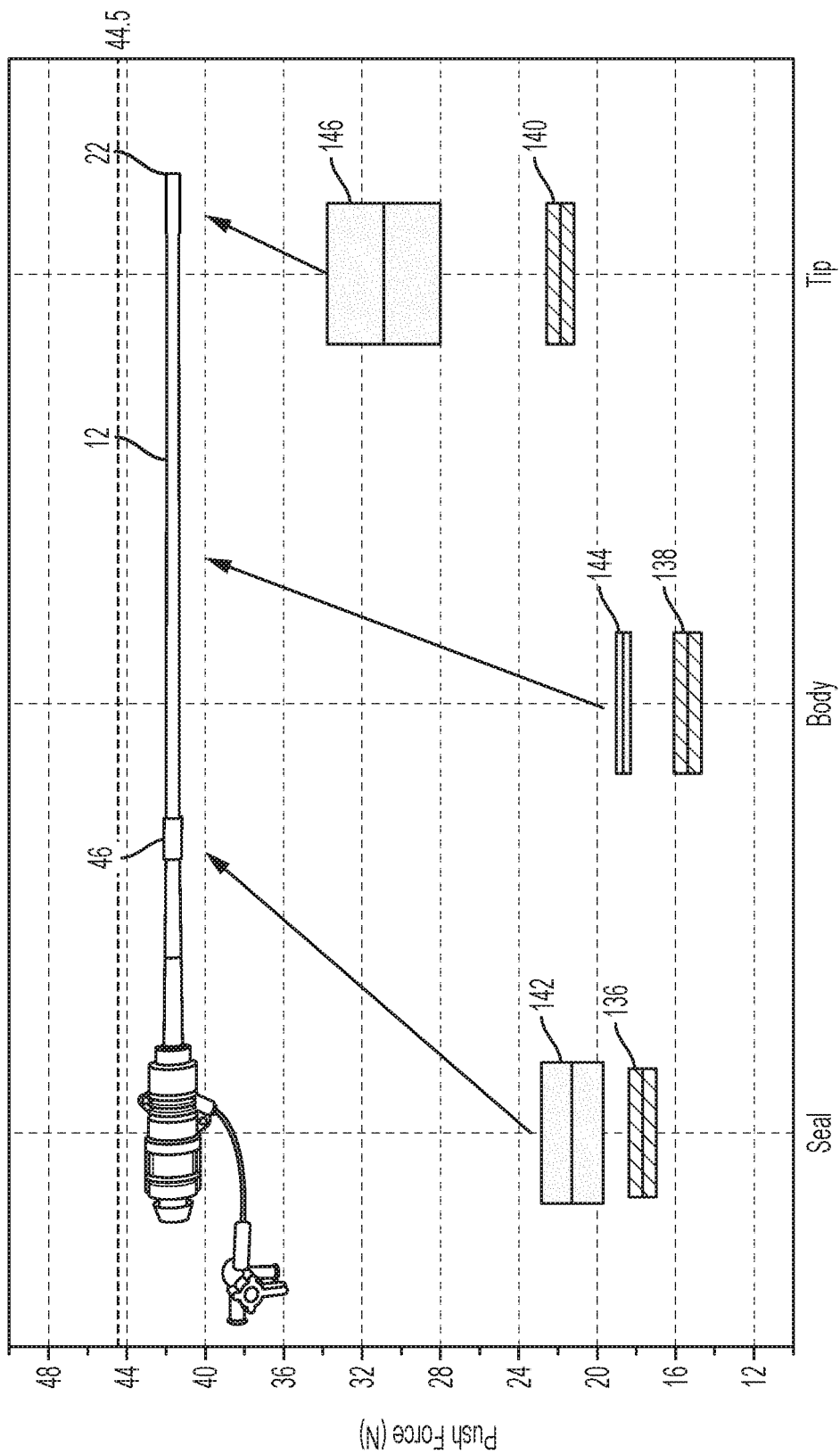
FIG. 17 illustrates a chart of reduced push force of the delivery apparatus through an expanded sheath of the system, according to an embodiment of the present disclosure.

FIG. 17 illustrates a chart of reduced push force of the delivery apparatus through an expanded sheath 12 of the system. The vertical axis of the chart displays push force in Newtons. The horizontal axis corresponds to select portions of the sheath 12 (the seal 46, the body of the sheath 12 between the seal and the tip, and the tip at the distal end 22 of the sheath 12).

The lower bars 136, 138, 140 in the chart correspond to the push force required for a delivery apparatus through a sheath that has been pre-expanded according to the systems, apparatuses, and methods of the present disclosure. The bar 136 corresponds to the push force required at the seal 46. The bar 138 corresponds to the push force required through the body of the sheath 12 between the seal and the tip. The bar 140 corresponds to the push force required through the tip at the distal end 22 of the sheath 12.

The upper bars 142, 144, 146 in the chart correspond to the push force required for a delivery apparatus through an expandable sheath that has not been pre-expanded according to the present disclosure. The bar 142 corresponds to the push force required at a seal of the unexpanded sheath. The bar 144 corresponds to the push force required through the body of the unexpanded sheath between the seal and the tip. The bar 146 corresponds to the push force required through the tip at a distal end of the unexpanded sheath.

The push force is shown to reduce for the pre-expanded sheath according to the systems, apparatuses, and methods of the present disclosure. The push force at the seal 46 is approximately 15% less for the pre-expanded sheath according to the present disclosure (about 18N versus 21N). The push force through the body of the unexpanded sheath between the seal and the tip is approximately 18% less for the pre-expanded sheath according to the present disclosure (about 15.5N versus 19N). The push force at the tip at a distal end of the unexpanded sheath is approximately 27% less for the pre-expanded sheath according to the present disclosure (about 22.5N versus 31N).

Accordingly, the systems, apparatuses, and methods of the present disclosure may result in a reduced push force for a delivery apparatus, as well as reducing a number of steps performed during a medical procedure, among other beneficial results.

FIGS. 14A-16C illustrate variations of embodiments of systems for introducing a delivery apparatus into a patient's vasculature. The features of the embodiments of FIGS. 14A-16C may be utilized with or applied to the embodiments of FIGS. 1-13B, and the features of the embodiments of FIGS. 1-13B may be utilized with or applied to the embodiments of FIGS. 14A-16C.

Figure 14A:
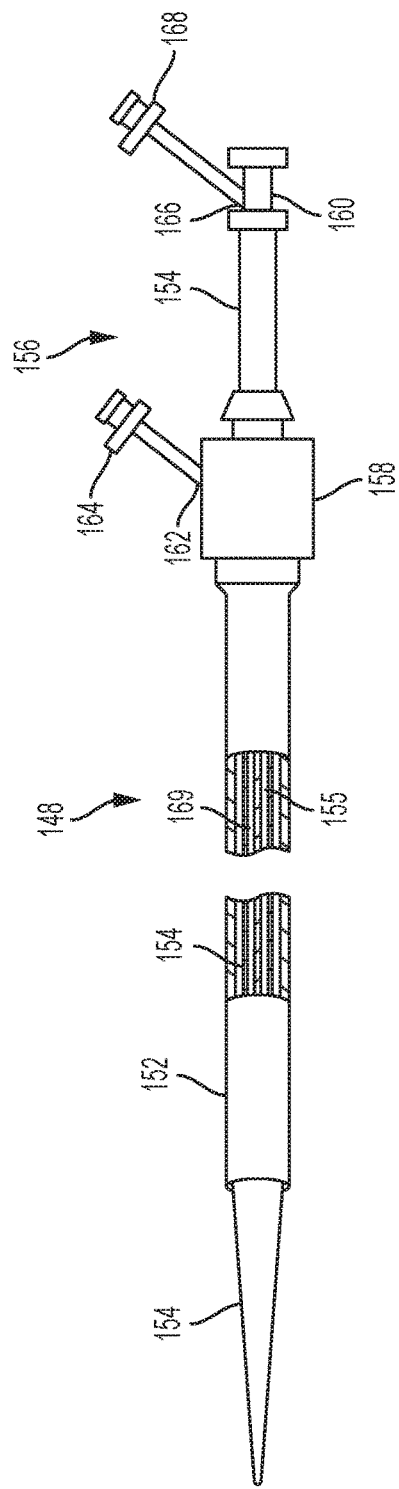
FIG. 14A illustrates a side view of a system according to an embodiment of the present disclosure, with a portion cut away.

FIGS. 14A, B, and C illustrate an embodiment of a system 148 in which the plug 150 comprises an inflatable body. The plug 150 may comprise an expandable portion of the introducer 154 that is coupled to the introducer 154. The system includes a sheath 152, and an introducer 154. The sheath 152 may be configured similarly as the sheath 12 in the embodiments of FIGS. 1-13B. The system may include a control housing 156 that may be positioned at a proximal end of the system and may include a sheath housing 158 and an introducer housing 160. A fluid port 162 may couple to the sheath housing 158 for passing fluid through the sheath 152. Tubing 164 may be coupled to the fluid port 162 for passing fluid through the fluid port 162, and may include a valve for sealing flow of the fluid through the fluid port 162. A fluid port 166 may couple to the introducer housing 160 for passing fluid through the introducer 154 and to the plug 150. Tubing 168 may be coupled to the fluid port 166 for passing fluid through the fluid port 166, and may include a valve for sealing flow of the fluid through the fluid port 166. The sheath 152 and introducer 154 may be inserted into the patient's vasculature in a similar manner as the system discussed in regard to FIGS. 1-13B.

FIG. 14A illustrates the system in an insertion configuration, in which the introducer 154 is positioned within the sheath 152 and the plug 150 and introducer 154 are in an insertion position within the sheath 152. The plug 150 is flattened, or in an unexpanded configuration or undeployed configuration, within the sheath 152. The sheath housing 158 and introducer housing 160 may be locked in position relative to each other to lock the corresponding sheath 152 and introducer 154 in position relative to each other and to secure the plug 150 within the lumen of the sheath 152.

A cut-away portion of the sheath 152 and introducer 154 is shown in FIG. 14A. The introducer 154 may include an internal lumen 169 configured to convey a fluid or other material to or from the plug 150. The internal lumen 169 may be utilized to inflate the plug 150 with fluid, which may be provided by the fluid port 166 and tubing 168. The introducer 154 may also include an internal channel 155, similar to the channel 116 of the introducer 14, for receiving a guide wire.

Figure 14B:
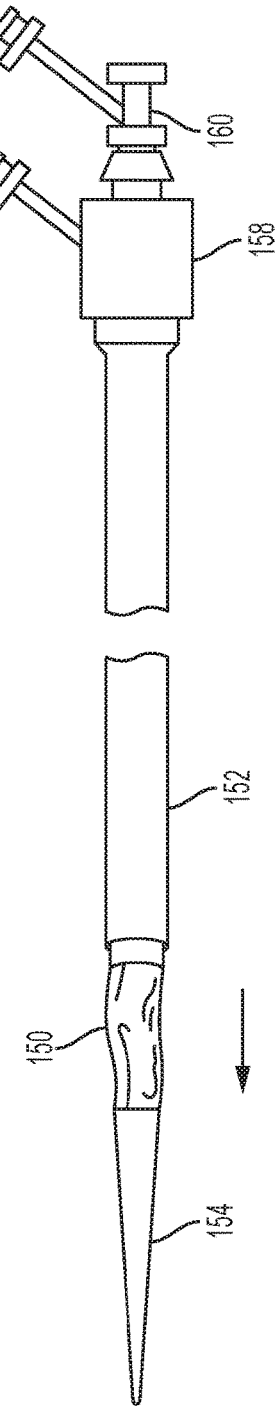
FIG. 14B illustrates a side view of the system shown in FIG. 14A.

FIG. 14B illustrates the system in an advanced configuration, in which the introducer is advanced distally through the sheath 152 and the plug 150 is exterior of the sheath 152. The plug 150 and introducer 154 are in an advanced position distal of the sheath 152. The plug 150 is flattened, or in an unexpanded configuration or undeployed configuration. The plug 150 may be in the first position, which may be a deflated state of the plug 150. The introducer housing 160 may be advanced distally towards the sheath housing 158 to advance and expose the plug 150.

In the advanced position, the plug 150 may be inflated to move to the second position and increase the diameter of the plug 150.

Figure 14C:
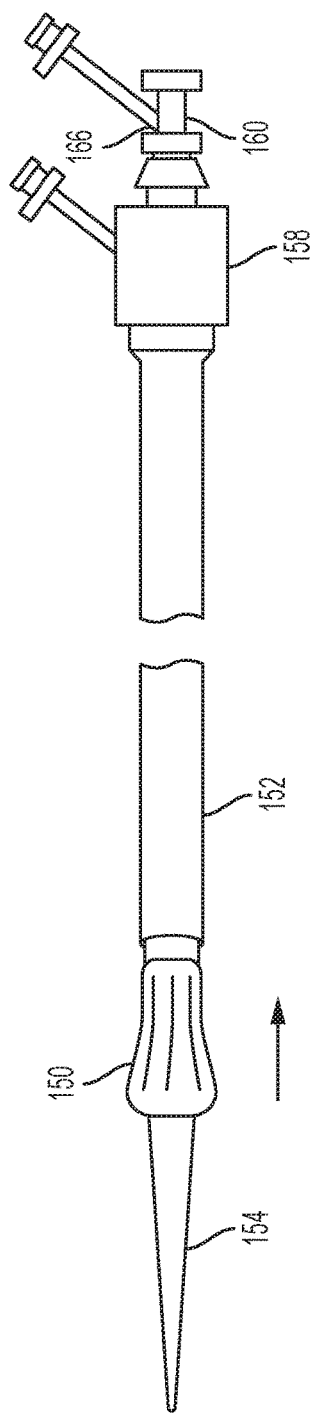
FIG. 14C illustrates a side view of the system shown in FIG. 14A.

FIG. 14C illustrates the plug 150 inflated to the second position, or the expanded configuration, or deployed configuration. The plug 150 in the second position has a length that is less than the length of the sheath 152 and has a diameter that is larger than the interior diameter of the sheath 152. The plug 150 may extend radially outward from the introducer 154. The plug 150 may comprise an inflatable body such as a balloon. The plug 150 may have a tapered shape that tapers outward from a proximal portion of the plug 150 to a distal portion of the plug 150. The plug 150 may have a conical shape to ease entry into the sheath 152 when the plug 150 is pulled proximally. The plug 150 may be activated to the second position by being inflated via fluid passing through the fluid port 166.

The plug 150 may be pulled through the sheath 152 in a similar manner as discussed in regard to FIGS. 1-13B. The plug 150, when retracted or withdrawn through the sheath 152 serves to expand the sheath 152 in a similar manner as discussed in regard to FIGS. 1-13B. A transient expansion may result, as discussed in regard to the embodiments of FIGS. 1-13B.

FIGS. 15A, B, and C, illustrate an embodiment of a system in which the plug 170 comprises a bellows structure. The system includes a sheath 172 and an introducer 174. The sheath 172 may be configured similarly as the sheath 12 in the embodiments of FIGS. 1-13B. The plug 170 may comprise an expandable portion of the introducer 174 that is coupled to the introducer 174. The system may also include a control housing positioned at a proximal end of the system and may include a sheath housing and an introducer housing in a similar manner as discussed in regard to FIGS. 1-13B.

FIG. 15A illustrates a close-up view of the distal end 176 of the sheath 172, with a portion cut-away. The introducer 174 may include an inner shaft 171 and an outer shaft 173 in a similar manner as discussed in regard to FIGS. 1-13B. The inner shaft 171 may include an internal channel 175, similar to the channel 116 of the introducer 14, for receiving a guide wire.

The plug 170 may be integral with the outer shaft 173. The introducer 174 may include a thicker portion 177 coupled to the thinner portion (represented by inner shaft 171) at a step 179.

The plug 170 may comprise a plurality of supports 178 separated by respective pivot portions 180. The supports 178 may comprise walls and the pivot portions 180 may comprise creases between the walls. The supports 178 may be coupled to the outer shaft 173 of the introducer 174 in a similar manner as the supports 80 of the plug 78 in FIGS. 1-13B.

The introducer 174 and plug 170 may be positioned within the lumen of the sheath 172 in an insertion configuration, for insertion together into the patient's vasculature. The plug 170 and introducer 174 may be in an insertion position within the sheath 172. The plug 170 may be flattened, or in an unexpanded configuration or undeployed configuration. The plug 170 may be in the first position.

FIG. 15A illustrates the system in the advanced configuration. The introducer 174 and plug 170 may move to an advanced position, distal of the distal end 176 of the sheath 172 in a similar manner as discussed in regard to the embodiments of FIGS. 1-13B. The plug 170 is positioned exterior of the lumen of the sheath 172. The plug 170 remains in the first position, and is flattened or in an undeployed or unexpanded configuration.

FIG. 15B illustrates the plug 170 in the second position, or in an expanded configuration, or deployed configuration. The plug 170 has compressed such that the supports 178, in the form of walls, bend to increase the diameter of the plug 170. The supports 178 bend to move the plug 170 from the first position to the second position. The supports 178 extend radially outward from the introducer 174. The extension of the supports 178 outward from the introducer 174 increases the diameter of the plug 170 to be greater than the interior diameter of the sheath 172. The plug 170 may be activated from the first position to the second position by the force of the thicker portion 177 or step 179 against the plug 170, in a similar manner as discussed in regard to the embodiments of FIGS. 1-13B. The plug 170 in the second position has a length that is less than the length of the sheath 172.

FIG. 15C illustrates the plug 170 retracted or withdrawn through the sheath 172. The plug 170 may be pulled through the sheath 172 in a similar manner as discussed in regard to FIGS. 1-13B. The plug 170, when pulled through the sheath 172 serves to expand the sheath 172 in a similar manner as discussed in regard to FIGS. 1-13B. A transient expansion may result, as discussed in regard to the embodiments of FIGS. 1-13B.

Figure 16A:
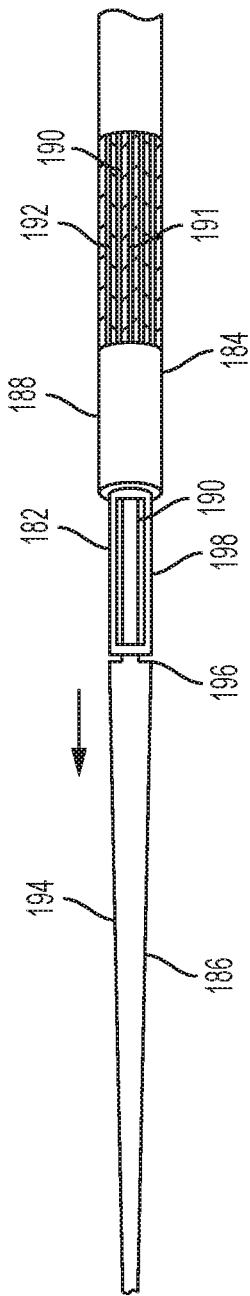
FIG. 16A illustrates a side view of a portion of a system according to an embodiment of the present disclosure, with a portion cut away.

FIGS. 16A, B, and C, illustrate an embodiment of a system in which the plug 182 comprises a self-expanding structure. The system includes a sheath 184 and an introducer 186. The sheath 184 may be configured similarly as the sheath 12 in the embodiments of FIGS. 1-13B. The plug 182 may comprise an expandable portion of the introducer 186 that is coupled to the introducer 186. The system may also include a control housing positioned at a proximal end of the system and may include a sheath housing and an introducer housing in a similar manner as discussed in regard to FIGS. 1-13B.

FIG. 16A illustrates a close-up view of the distal end 188 of the sheath 184, with a portion cut-away. The introducer 186 may include an inner shaft 190 and an outer shaft 192 in a similar manner as discussed in regard to FIGS. 1-13B. The inner shaft 190 may include an internal channel 191, similar to the channel 116 of the introducer 14, for receiving a guide wire. The plug 182 may be integral with the outer shaft 192. The introducer 186 may include a thicker portion 194 coupled to the thinner portion (represented by inner shaft 190) at a step 196.

The plug 182 may comprises a plurality of supports 198 slidably disposed along the inner shaft 190. The supports 198 may comprise arms and may be made of a self-expanding material such as nitinol. The self-expanding material may be configured to automatically expand upon being moved exterior of the lumen of the sheath 184. Nitinol, for example, may respond to the patient's body heat to transform into an expanded configuration upon being moved exterior of the lumen of the sheath 184. The supports 198 may be coupled to the outer shaft 192 of the introducer 186 in a similar manner as the supports 80 of the plug 78 in FIGS. 1-13B.

The introducer 186 and plug 182 may be positioned within the lumen of the sheath 184 in an insertion configuration, for insertion together into the patient's vasculature. The plug 182 and introducer 186 may be in an insertion position within the sheath 184. The plug 182 may be flattened, or in an unexpanded configuration or undeployed configuration. The plug 182 may be in the first position.

FIG. 16A illustrates the system in the advanced configuration. The introducer 186 and plug 182 may be moved to an advanced position distal of the distal end 188 of the sheath 184 in a similar manner as discussed in regard to the embodiments of FIGS. 1-13B. The plug 182 is positioned exterior of the lumen of the sheath 184. The plug 182 remains in the first position, and is flattened or in an undeployed or unexpanded configuration.

Figure 16B:
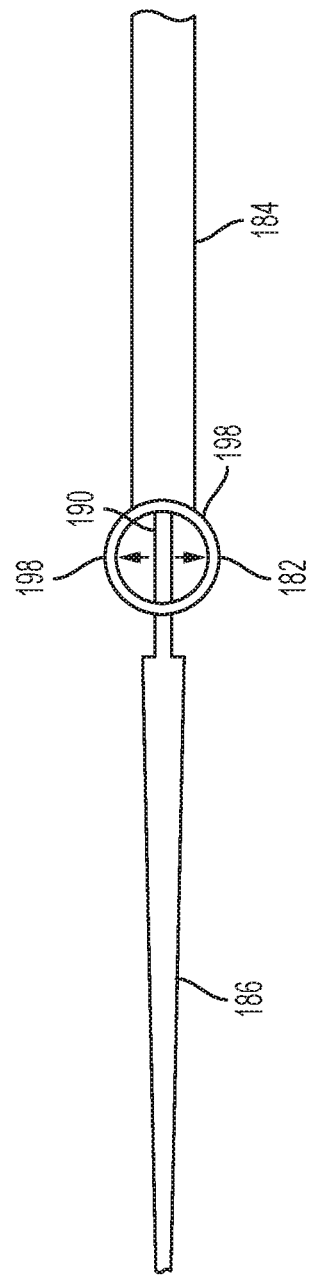
FIG. 16B illustrates a side view of the portion of system shown in FIG. 16A.

FIG. 16B illustrates the plug 182 in the second position, or in an expanded configuration, or deployed configuration. The supports 198 of the plug 182 have self-expanded to a larger configuration outward from the introducer 186 to increase the diameter of the plug 182 to be greater than the interior diameter of the sheath 184. The supports 198 extend radially outward from the introducer 186. The supports 198 bend to move the plug 182 from the first position to the second position. The plug 182 in the second position has a length that is less than the length of the sheath 184. The plug 182 may be activated from the first position to the second position by being moved exterior of the lumen of the sheath 184, and the plug 182 may self-expand to the second position.

Figure 16C:
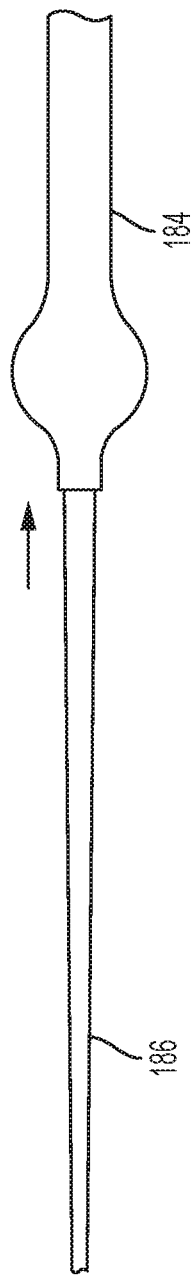
FIG. 16C illustrates a side view of the portion of system shown in FIG. 16A.

FIG. 16C illustrates the plug 182 retracted or withdrawn through the sheath 184. The plug 182 may be pulled through the sheath 184 in a similar manner as discussed in regard to FIGS. 1-13B. The plug 182, when pulled through the sheath 184 serves to expand the sheath 184 in a similar manner as discussed in regard to FIGS. 1-13B. A transient expansion may result, as discussed in regard to the embodiments of FIGS. 1-13B.

Figure 19:
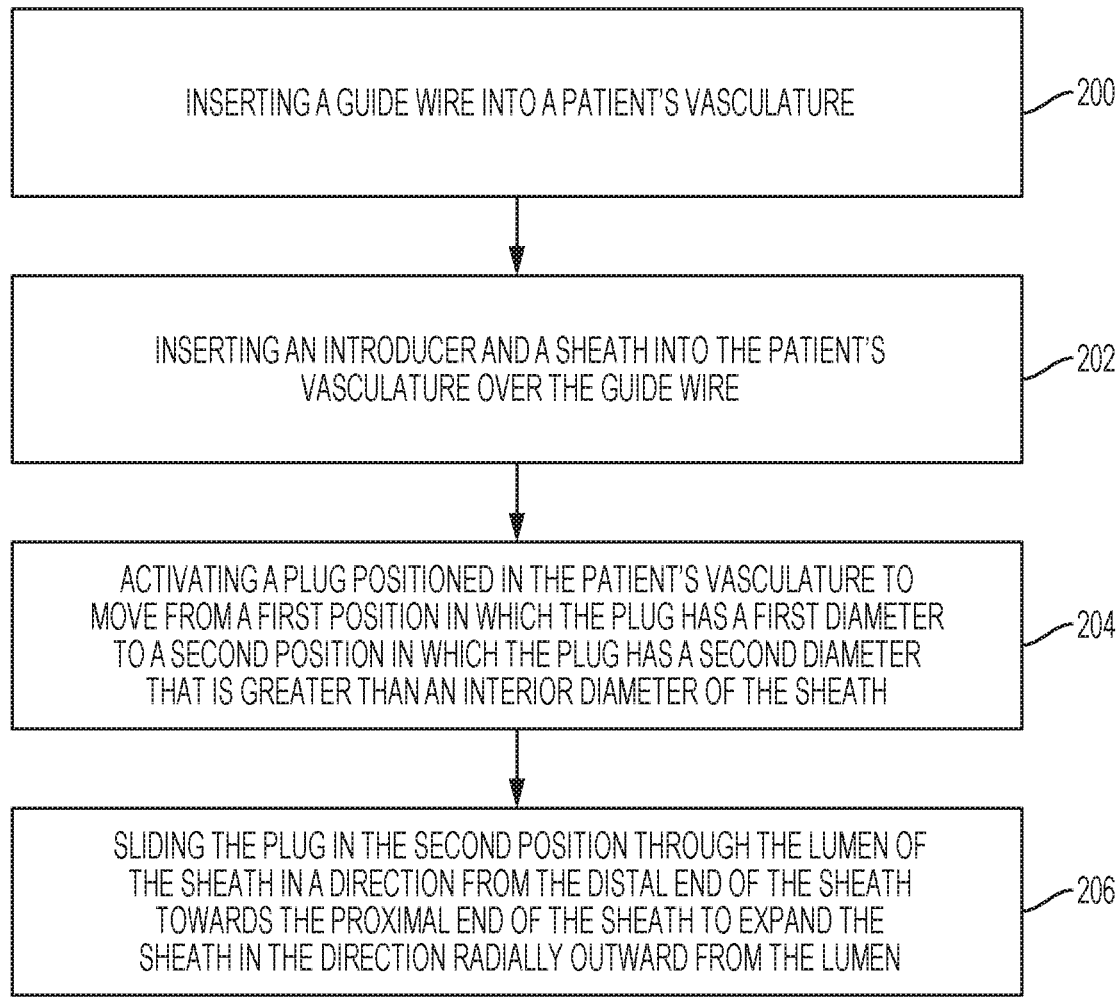
FIG. 19 illustrates a flow chart of a method, according to an embodiment of the present disclosure.

FIG. 19 illustrates a method that may utilize the systems and apparatuses disclosed herein. The method may comprise a method of pre-conditioning a sheath for introduction of a delivery apparatus therethrough. The method may first include a step 200 of inserting a guide wire into a patient's vasculature. The step may include accessing the patient's vasculature and passing the guide wire therein until reaching the desired position within the patient's body. The method may then include a step 202 of inserting an introducer and a sheath into the patient's vasculature over the guide wire. The introducer and sheath may be configured as the embodiments of the introducers and sheaths disclosed herein. The sheath may extend around the introducer and may have a distal end and a proximal end and may have a lumen, and may be configured to expand in a direction radially outward from the lumen. The introducer may be positioned within the lumen of the sheath upon introduction, as disclosed herein. The sheath and introducer may be in an insertion configuration, with the introducer and plug, or expandable portion of the introducer, in an insertion position within the lumen of the sheath. The plug, or expandable portion of the introducer, may be flattened or in an unexpanded or undeployed configuration within the lumen of the sheath upon insertion into the patient's vasculature.

The method may include a step 204 of activating the plug, or expandable portion of the introducer, positioned within the patient's vasculature to move from a first position in which the plug has a first diameter to a second position in which the plug has a second diameter that is greater than an interior diameter of the sheath. The step of activating may include any of the methods disclosed herein, including advancing the plug, or expandable portion of the introducer, beyond the distal end of the sheath and pressing against the plug, inflating the plug, or simply extending the plug beyond the distal end of the sheath in a self-expanding embodiment (e.g., an embodiment using nitinol or the like), including other methods of activation.

The method may include a step 206 of sliding the plug, or the expandable portion of the introducer, through the lumen of the sheath in a direction from the distal end of the sheath towards the proximal end of the sheath to expand the sheath in the direction radially outward from the lumen. The plug, or expandable portion of the introducer, is in the second position with a diameter greater than the interior diameter of the sheath. The expansion of the sheath may comprise a transient expansion, as disclosed herein.

Additional steps may include introducing a delivery apparatus through the pre-expanded sheath, in a manner disclosed herein.

The steps of the method may be modified, excluded, or added to, with systems, apparatuses, and methods disclosed herein. Methods are not limited to the method described in regard to FIG. 19, and may also include any other means or methods disclosed herein.

The embodiments of systems, apparatuses, and methods disclosed herein may be modified or combined as desired. The sheaths disclosed herein may have a variety of shapes, including a cylindrical cross section, rectangular cross section, or other shape, for example a hexagonal cross section or other shape. The introducers disclosed herein may have a variety of shapes with a different structure than disclosed herein. The means for activating the plug may be varied, for example the configuration of locks in the introducer housing may be varied or a different apparatus for activating the plug may be used. The configuration of the housings disclosed herein may be varied, or may be excluded in certain embodiments.

Any of the systems, apparatuses, and methods disclosed herein may be modified to utilize self-expanding materials or structures, such as nitinol. For example, the plug 78 described in regard to FIGS. 1-13B may be modified to be self-expanding, and utilize a material such as nitinol.

The materials used in the sheaths and introducers and plugs disclosed herein may be varied as desired. The introducers may be made of HDPE or LDPE or other materials as desired. The plugs, or expandable portions of the introducers, may be made of nylon, HDPE, a shape memory material (such as nitinol), ABS, PEBAX, or urethane, or other materials.

The sizes of the sheaths utilized may be varied as desired. In one embodiment a 14-F sheath, with a 5.9 millimeter outer diameter may be utilized. In other embodiments, a lesser or greater outer diameter may be utilized. A 16-F, 18-F, or 20-F size sheath, or other size sheath may be utilized as desired. In one embodiment, a sheath having a length of 36 centimeters, or a lesser or greater length may be utilized.

The features of the sheaths may be implemented independently of the introducers, which may also be implemented independently of the plugs. The various apparatuses of the system may be implemented independently.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of systems, apparatuses, and methods as disclosed herein, which is defined solely by the claims. Accordingly, the systems, apparatuses, and methods are not limited to that precisely as shown and described.

Certain embodiments of systems, apparatuses, and methods are described herein, including the best mode known to the inventors for carrying out the same. Of course, variations on these described embodiments will become apparent to those of ordinary skill in the art upon reading the foregoing description. The inventor expects skilled artisans to employ such variations as appropriate, and the inventors intend for the systems, apparatuses, and methods to be practiced otherwise than specifically described herein. Accordingly, the systems, apparatuses, and methods include all modifications and equivalents of the subject matter recited in the claims appended hereto as permitted by applicable law. Moreover, any combination of the above-described embodiments in all possible variations thereof is encompassed by the systems, apparatuses, and methods unless otherwise indicated herein or otherwise clearly contradicted by context.

Groupings of alternative embodiments, elements, or steps of the systems, apparatuses, and methods are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses an approximation that may vary, yet is capable of performing the desired operation or process discussed herein.

The terms "a," "an," "the" and similar referents used in the context of describing the systems, apparatuses, and methods (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the systems, apparatuses, and methods and does not pose a limitation on the scope of the systems, apparatuses, and methods otherwise claimed. No language in the present specification should be construed as indicating any non-claimed element essential to the practice of the systems, apparatuses, and methods.

All patents, patent publications, and other publications referenced and identified in the present specification are individually and expressly incorporated herein by reference in their entirety for the purpose of describing and disclosing, for example, the compositions and methodologies described in such publications that might be used in connection with the systems, apparatuses, and methods. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A system for introducing a delivery apparatus into a patient's vasculature, the system comprising:
    a sheath having a distal end, a proximal end, an interior diameter, a lumen, and a length extending from the distal end to the proximal end, the sheath being configured to be inserted into the patient's vasculature and to expand in a direction radially outward from the lumen;
an introducer configured to be positioned within the lumen of the sheath to introduce the sheath into the patient's vasculature, the introducer having a channel for receiving a guide wire;
an inflatable plug coupled to the introducer and configured to move from a first position in which the inflatable plug has a first diameter to a second position that is a maximum expanded state of the inflatable plug and in which the inflatable plug is inflated with fluid and has a second diameter that is greater than the first diameter and greater than the interior diameter of the sheath, the inflatable plug in the first position being configured to fit within the lumen, and the inflatable plug in the second position having a length that is less than the length of the sheath and being configured to slide within the lumen while inflated with the fluid and at the maximum expanded state in a direction from the distal end of the sheath towards the proximal end of the sheath to expand the sheath in the direction radially outward from the lumen; and
a fluid lumen for conveying fluid to the inflatable plug to move the inflatable plug to the second position.

2. The system of claim 1, wherein the sheath is elastic and biased in a direction radially towards the lumen of the sheath.

3. The system of claim 1, wherein the introducer has a distal end and a proximal end and a length extending from the distal end to the proximal end, the length of the introducer being greater than the length of the sheath.

4. The system of claim 1, wherein the distal end of the sheath includes an opening configured for the introducer and the inflatable plug to pass therethrough.

5. The system of claim 4, wherein the inflatable plug is positioned on the introducer such that the inflatable plug moves from the first position to the second position at a position distal to the opening of the sheath when the introducer is positioned within the lumen of the sheath.

6. The system of claim 4, wherein the inflatable plug is coupled to the introducer such that withdrawal of the introducer through the lumen of the sheath in the direction from the distal end of the sheath towards the proximal end of the sheath causes the inflatable plug in the second position to enter the opening of the sheath and slide within the lumen of the sheath to transiently expand the sheath in the direction radially outward from the lumen of the sheath.

7. The system of claim 1, wherein the inflatable plug in the second position extends radially outward from the introducer.

8. The system of claim 1, wherein the introducer is configured to be coupled to the sheath upon insertion of the sheath and the introducer together into the patient's vasculature.

9. The system of claim 8, wherein a proximal end of the introducer is configured to be coupled to the proximal end of the sheath upon insertion of the sheath and the introducer together into the patient's vasculature.

10. The system of claim 9, further comprising:
an introducer housing positioned at the proximal end of the introducer; and
a sheath housing positioned at the proximal end of the sheath and configured to be coupled to the introducer housing upon insertion of the sheath and the introducer together into the patient's vasculature.

11. The system of claim 10, wherein at least a portion of the introducer housing is configured to slide distally for a defined length relative to the sheath housing to position the inflatable plug at a defined distance distal of the distal end of the sheath.

12. The system of claim 10, further comprising a coupler for coupling the introducer housing to the sheath housing, the coupler configured to hold the introducer housing and the sheath housing in position relative to each other upon insertion of the sheath and the introducer together into the patient's vasculature.

13. The system of claim 1, wherein the sheath and the introducer are configured to be held in position relative to each other upon insertion of the sheath and the introducer together into the patient's vasculature.

14. The system of claim 1, wherein the inflatable plug has a conical shape in the second position.

15. The system of claim 14, wherein the inflatable plug in the second position tapers outward from a proximal portion of the inflatable plug to a distal portion of the inflatable plug.

16. The system of claim 1, wherein the inflatable plug is deflated in the first position and is inflated with the fluid to expand radially outward from the first position to the second position, the second position comprising a deployed configuration of the inflatable plug, the inflatable plug configured to slide within the lumen of the sheath while in the deployed configuration to expand the sheath in the direction radially outward from the lumen of the sheath.

17. A system for introducing a delivery apparatus into a patient's vasculature, the system comprising:
a sheath having a distal end, a proximal end, an interior diameter, a lumen, and a length extending from the distal end to the proximal end, the sheath being configured to be inserted into the patient's vasculature and to expand in a direction radially outward from the lumen;
an introducer having a channel for receiving a guide wire and being configured to be positioned within the lumen of the sheath, the introducer having an expandable portion including a plurality of supports, the expandable portion configured to move from a first position in which the plurality of supports are flattened and have a first diameter to a second position in which the plurality of supports extend radially outward from the introducer and have a second diameter that is larger than the first diameter and the interior diameter of the sheath, the expandable portion being configured to slide within the lumen in the second position to expand the sheath in the direction radially outward from the lumen.

18. The system of claim 17, wherein the introducer includes an inner shaft and an outer shaft, and the expandable portion is integral with the outer shaft.

19. The system of claim 17, wherein the introducer has a distal end and a proximal end and a length extending from the distal end to the proximal end, and the length of the introducer is greater than the length of the sheath.

20. The system of claim 17, wherein the expandable portion is positioned on the introducer such that the expandable portion moves from the first position to the second position exterior of the sheath when the introducer is positioned within the lumen.

* * * * *